United States Patent
Raz

(10) Patent No.: US 6,498,148 B1
(45) Date of Patent: Dec. 24, 2002

(54) IMMUNIZATION-FREE METHODS FOR TREATING ANTIGEN-STIMULATED INFLAMMATION IN A MAMMALIAN HOST AND SHIFTING THE HOST'S ANTIGEN IMMUNE RESPONSIVENESS TO A TH1 PHENOTYPE

(75) Inventor: Eyal Raz, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/235,742

(22) Filed: Jan. 21, 1999

Related U.S. Application Data

(63) Continuation of application No. 08/927,120, filed on Sep. 5, 1997, now abandoned.

(51) Int. Cl.⁷ .......................... A01N 43/04; C12Q 1/68; C12N 15/63; C12P 19/34; C07H 21/02

(52) U.S. Cl. .......................... 514/44; 435/6; 435/91.1; 435/435; 536/23.1

(58) Field of Search ........................... 435/6, 91.1, 325, 435/354, 366; 514/44; 536/23.1

(56) References Cited

U.S. PATENT DOCUMENTS

| | | |
|---|---|---|
| 1,234,718 A | 9/1917 | Hilleman et al. |
| 3,725,545 A | 4/1973 | Maes |
| 3,906,092 A | 9/1975 | Hilleman et al. |
| 5,268,365 A | 12/1993 | Rudolph et al. |
| 5,276,019 A | 1/1994 | Cohen et al. |
| 5,278,302 A | 1/1994 | Caruthers et al. |
| 5,453,496 A | 9/1995 | Caruthers et al. |
| 5,580,859 A | 12/1996 | Felgner et al. |
| 5,663,153 A | 9/1997 | Hutcherson |
| 5,703,055 A | 12/1997 | Felgner et al. |
| 5,750,666 A * | 5/1998 | Caruthers et al. .......... 536/23.1 |
| 5,804,566 A | 9/1998 | Carson et al. |
| 5,849,719 A * | 12/1998 | Carson et al. ................ 514/44 |
| 6,194,388 B1 | 2/2001 | Krieg et al. |
| 6,207,646 B1 * | 3/2001 | Krieg et al. ................... 514/44 |
| 6,239,116 B1 | 5/2001 | Krieg et al. |

FOREIGN PATENT DOCUMENTS

| | | | |
|---|---|---|---|
| EP | 468520 | 1/1992 | |
| EP | 855184 | 1/1997 | |
| WO | WO 95/05853 | 3/1995 | |
| WO | WO 95/26204 | 10/1995 | |
| WO | WO 96/02555 A1 | 2/1996 | |
| WO | WO 97/28259 A1 * | 7/1997 | .................. 514/44 |
| WO | WO 97/28259 | 8/1997 | |
| WO | WO 98/16247 | 4/1998 | |
| WO | WO 98/18810 | 5/1998 | |
| WO | WO 98/52962 | 11/1998 | |

OTHER PUBLICATIONS

Hodes, R.J. T–Cell–Mediated Regulation: Help and Suppression, in Fundamental Immunology, Second Edition, edited by William E. Paul, Raven Press Ltd., New York 1989, pp. 587–620.*

Klinman, D.M. Contribution of CpG Motifs to the Immunogenicity of DNA Vaccines, J. Immunol. 158, 3635–3639 (1997).*

Hartmann et al. (2000) "Mechanism and Function of a Newly Identified CpG DNA Motif in Human Primary B Cells." *The Journal of Immunology*, vol. 164:944–952.

Hartmann et al. (2000) "Delineation of a CpG Phosphorothioate Oligodeoxynucleotide for Activating Primate Immune Responses In Vitro and In Vivo." *The Journal of Immunology*, vol. 164:1617–1624.

Liang et al. (1996) "Activation of Human B Cells by Phosphorothioate Oligodeoxynucleotides." *J. Clin. Invest.*, vol. 98(5):1119–1129.

Ballas et al. (1996). "Induction of NK Activity in Murine and Human Cells by CpG Motifs in Oligodeoxynucleotides and Bacterial DNA" *J. Immunol.*, vol. 157(5): 1840–1845.

Branda et al. (1993). "Immune Stimulation by an Antisense Oligomer Complementary to the rev Gene of HIV–1" *Biochem. Pharmacol.*, vol. 45: 2037–2043.

Branda et al. (1996). "Amplification of antibody production by phosphorothioate oligodeoxynucleotides" *J. Lab. Clin. Med.*, vol. 128: 329–338.

Chase et al. (1997). "Bacterial DNA–Induced NK Cell IFN–γ Production is Dependent on Macrophage Secretion of IL–12" *Clin. Immunol. and Immunopathol.* vol. 84(2): 185–193.

Cowdery et al. (1996). "Bacterial DNA induces NK ells to produce IFN–γ in vivo and increases the toxicity of lipopolysaccharides" *J. Immunol.*, vol. 156: 4570–4575.

Gray et al. (1997). "Immune cell involvement in anti–c–myc DNA prevention of tumor formation in a mouse model of Burkitt's lymphoma" *Nucleosides & Nucleotides*, vol. 16(7–9): 1727–1730.

(List continued on next page.)

Primary Examiner—Sean McGarry
Assistant Examiner—Jane Zara
(74) *Attorney, Agent, or Firm*—Carol L. Francis; Paula A. Borden; Bozicevic, Field & Francis, LLP.

(57) ABSTRACT

The invention relates to methods for preventing or reducing antigen-stimulated, granulocyte-mediated inflammation in tissue of an antigen-sensitized mammal host by delivering an immunostimulatory oligonucleotide to the host. In addition, methods for using the immunostimulatory oligonucleotides to boost a mammal host's immune responsiveness to a sensitizing antigen (without immunization of the host by the antigen) and shifting the host's immune responsiveness to a Th1 phenotype to achieve various therapeutic ends are provided. Kits for practicing the methods of the invention are also provided.

19 Claims, 11 Drawing Sheets

OTHER PUBLICATIONS

Hsu et al. (1996). "Immunoprophylaxis of allergen–induced immunoglobulin E synthesis and airway hyperresponsivem\ness in vivo by genetic immunization" *Nature Med.*, vol. 2(5): 540–544.

Kataoka et al. (1992). "Antitumor Activity of Synthetic Oligonucleotides with Sequences form cDNA Encoding Proteins of *Mycobacterium bovis* BCG" *Jpn. J. Cancer Res.*, vol. 83: 244–247.

Kimura et al. (1994). "Binding of oligoguanylate to scavenger receptors is required for oligonucleotides to augment NK cell activity and induce IFN" *J. Biochem.*, vol. 116: 991–994.

Kline et al. (1997). "Immune redirection by CpG oligonucleotides: conversion of a Th2 response to a Th1 response in a murine model of asthma" *J. Invest. Med.*, vol. 45(3): 282A.

Klinman et al. (1996). "CpG Mofits Present in Bacterial DNA Rapidly Induce Lymphocytes to Secrete Interleukin 6, Interleukin 12, and Interferon γ" *Proc. Natl. Acad. Sci. USA.*, vol. 93: 2879–2883.

Klinman et al. (1997). "Contribution of CpG mofits to the immunogenicity of DNA vaccines" *J. Immunol.*, vol. 158: 3635–3639.

Krieg et al. (1989). "A Role for Endogenous Retroviral Sequences in the Regulation of Lymphocyte Activation" *J. Immunol.*, vol. 143(8): 2448–2451.

Krieg et al. (1995). "CpG Mofits in Bacterial DNA Trigger Direct B–cell Activation" *Nature*, vol. 374: 546–549.

Krieg et al. (1996). "Lymphocyte activation by CpG dinucleotide motifs in prokaryotic DNA" *Trends Microbiol.*, vol. 4(2): 73–76.

Krieg et al. (1996). "Oligonucleotide modifications determine the magnitude of B cell stimulation by CpG motifs" *Antisense Nucleic Acid Drug Dev.*, vol. 6: 133–139.

Kuramoto et al. (1992). "Oligonucleotide sequences required for natural killer cell activation" *Jpn. J. Cancer Res.*, vol. 83: 1128–1131.

Leclerc et al. (1997). "The preferential induction of a Th1 immune response by DNA based immunization is mediated by the immunostimulatory effect of plasmid DNA" *Cell. Immunol.*, vol. 179: 97–106.

Lipford et al. (1997). "CpG–containing synthetic oligonucleotides promote B and cytotoxic T cell responses to protein antigen: a new class of vaccine adjuvnat" *Eur. J. immunol.*, vol. 27: 2340–2344.

Mojcik et al. (1993). "Administration of a Phosphorothioate Oligonucleotide antisense to Murine Endogenous Retroviral MCF env Causes Immune Effects in Vivo in a Sequence–Specific Manner" *Clin. Immuno. And Immunopathol.*, vol. 67(2): 130–136.

Pisetsky et al. (1994). "Stimulation of Murine Lymphocyte Proliferation by a Phosphorothioate Oligonucleotide with Antisense Activity for herpes Simplex Virus" *Life Sci.*, vol. 54(2): 101–107.

Pisetsky (1995). "The immunologic properties of DNA" *J. Immunol.*, vol. 156(2): 421–423.

Pisetsky (1995). "Immunological properties of bacterial DNA" *Ann. N.Y. Acad. Sci.*, vol. 772: 152–163.

Pisetsky (1996). "Immune activation by bacterial DNA: a new genetic code" *immunity*, vol. 5: 303–310.

Ramsay et al. (1997). "DNA immunization" *Immunology and Cell Biology*, vol. 75: 360–363.

Raz et al. (1994). "Intradermal gene immunization: The possible role of DNA uptake in the induction of cellular immunity to viruses" *Proc. Natl. Acad. Sci. USA*, vol. 91: 9519–9523.

Raz et al. (1996). "Preferential induction of a $Th_1$ immune response and inhibition of specific IgE antibody formation by plasmid DNA immunization" *Proc. Natl. Acad. Sci. USA*, vol. 93: 5141–5145.

Roman et al. (1997). "Immunostimulatory DNA Sequences Function as T helper–1–promoting Adjuvants" *Nat. Med.*, vol. 3: 849–854.

Sato et al. (1996). "Immunostimulatory DNA sequences Necessary for Effective Intradermal Gene Immunization" *Science*, vol. 273: 352–354.

Schwartz et al. (1997). "CpG Mofits in bacterial DNA Cause Inflammation in the Lower Respiratory Tract" *J. Clin. Invest.*, vol. 100: 68–73.

Sonehara et al. (1996). "Hexamer Palindromic Oligonucleotides with 5'–CG–3' Motif(s) Induce Production of Interferon" *Journal of Interferon and Cytokine Research*, vol. 16: 799–803.

Sparwasser et al. (1997). "Macrophages sense pathogens via DNA motifs: induction of tumor necrosis factor–α–mediated shock" *Eur. J. Immunol.*, vol. 27: 1671–1679.

Stacey et al. (1996). "Macrophages ingest and are activated by bacterial DNA" *J. Immunol.*, vol. 157: 2116–2122.

Tokunaga et al. (1992). "Synthetic Oligonucleotides with Particular Base sequences from the cDNA Encoding Proteins on *Mycobacterium bovis* BCG Induce Interferons and Activate Natural Killer Cells" *Microbiol. Immunol.*, vol. 36(1): 55–66.

Weiner et al. (1997). "Immunostimulatory oligodeoxynucleotides containing the CpG motif are effective as immune adjuvants in tumor antigen immunization" *Proc. Natl. Acad. Sci. USA*, vol. 94: 10823–10837.

Whalen et al. (1995). "DNA–mediated immunization to the hepatitis B surface antigen" *Ann. N.Y. Acad. Sci.*, vol. 772: 64–76.

Yamamoto et al. (1992). "Unique Palindromic Sequences in Synthetic Oligonucleotides are Required to Induce INF and Augment INF–Mediated Natural Killer Activity" *J. Immunol.*, vol. 148: 4072–4076.

Yamamoto et al. (1994). "Ability of Oligonucleotides with Certain Palindromes to Induce Interferon Production and Augment Natural Killer Cell Activity is Associated with their Base Length" *Antisense Research and Development*, vol. 4: 119–122.

Yamamoto et al. (1994). "Synthetic oligonucleotides with certain Palindromes stimulate interferon production of human peripheral blood lymphocytes" *Jpn. Cancer Res.* vol. 85: 775–779.

Yamamoto et al. (1994). "Lipofection of Synthetic Oligodeoxyribonucleotide having a palindromic sequence of AACGTT to murine splenocytes enhances interferon production and natural killer activity" *Microbiol. Immunol.*, vol. 38: 831–836.

Yi et al. (1996). "IFN–γ Promotes IL–6 and IgM Secretion in Response to CpG Motifs in Bacterial DNA and Oligodeoxynucleotides" *J. Immunol.*, vol. 156(2): 5589–564.

Yi et al. (1996). "Rapid Immune Activation by CpG Motifs in Bacterial DNA" *J. Immunol.*, vol. 157(12): 5394–5402.

Zhao et al. (1996). "Effect of different chemically modified oligonucleotides in immune stimulation" *Biochem. Pharmacol.*, vol. 51(2): 173–182.

Bennett et al. (1985), "DNA Binding to Human Leukocytes." *The American Society for Clinical Investigation, Inc.* 2182–2190.

Carlberg (1993), "Rxr–independent Action of the Receptors for Thyroid Hormone, Retinoid Acid and Vitamin D on Inverted Palindromes." *Biochemical and Biophysical Research Communications*, vol. 195(3):1345–1353.

Corry et al. (1996), "Interleukin 4, but not Interleukin 5 or Eosinophils, Is Required in a Murine model of Acute Airway Hyperreactivity." *J. Exp. Med.*, vol. 183:109–117.

Davis et al. (1993), "Plasmid DNA Is Superior to Viral Vectors for Direct Gene Transfer into Adult Mouse Skeletal Muscle." *Human Gene Therapy*, vol. 4:733–740.

Ewel et al. (1992), "Polyinosinic–Polycytidylic Acid complexed with Poly–L–lysine and Carboxymethylcellulose in Combination with Interleukin 2 in Patients with Cancer: Clinical and Immunological Effects." *Cancer Research*, vol. 52:3005–3010.

Feltquate et al. (1997), "Different T Helper Cell Types and Antibody Isotypes Generated by Salinea nd Gene Gun DNA Immunization." *The Journal of Immunology*, vol. 158:2278–2284.

Fuller et al. (1994), "A Qualitative Progression in HIV Type 1 Glycoprotein 120–Specific Cytotoic Celular and Humoral Immune Responses in Mice Receiving a DNA–Based Glycoprotein 120 Vaccine." *AIDS Research and Human Retrviruses*, vol. 10(11):1433–1441.

Hohlfeld et al. (1994), "The Immunobiology of Muscle." *Immunology Today*, vol. 15(6):269–274.

Iguchi–Ariga et al. (1989),"CpG methylation of the camp–responsive enhancer/promoter sequence TGACGTCA abolishes specific factor binding as well as transcriptional activation." *Genes & Development*, vol. 3:612–619.

Jachimczak et al. (1993), "The effect of transforming growth factor–$\beta_2$–specific phosphorothrioate–anti–sense oligodeoxynucleotides in reversing cellular immunosuppression in malignant glioma." *J. Neurosurg*, vol. 78:944–951.

Kemeny et al. (1992), "CD8+ T cells in allergy." *Allergy*, vol. 47:12–21.

Jyonouchi et al. (1993), "Immunomodulating Actions of Nucleotides: Enchancement of Immunoglobulin Production by Human Cord Blood Lymphocytes." *Pediatric Research*, vol. 34(5):565–571.

Krieg (1995), "CpG DNA: A Pathogenic Factor in Systemic Lupus Erythematosus?" *Journal of Clinical Immunology*, vol. 15(6):284–292.

Lee et al. (1997), "Inhibition of IgE antibody Formation by Plasid DNA Immunization Is Mediated by both CD4+ and CD8+ T Cells." *Int. Arch. Allergy Immunol*, Vol. 113:227–230.

Mader et al. (1993), "A steroid–inducible promoter for the controlled overexpression of cloned genes in eukaryotic cells." *Proc. Natl. Acad. Sci.*, vol. 90:5603–5607.

Manickan et al. (1997), "Enhancement of immune response to naked DNA vaccine by immunization with transfected dendritic cells." *Journal of Leukocyte Biology*, vol. 61(2):125–132.

Messina et al. (1991), "Stimulation of in vitro Murine Lymphocyte Proliferation by Bacterial DNA." *The Journal of Immunology*, vol. 147:1759–1764.

Nakagawa et al. (1993), "Immunotherapy of Allergic Diseases." *Int. Arch Allergy Immunology.*, vol. 102:117–120.

Nishida et al. (1990), "Definition of a GC–rich motif as regulatory sequence of the human IL–3 gene: coordinate regulation of the IL–3 gene by CLE/GC box of the GM–CSF gene in T cell activation." *International Immunology*, vol. 3(3):245–254.

Pardoll et al. (1995), "Exposing the Immunology of Naked DNA Vaccines." *Immunity*, vol. 3(2):165–169.

Ramsay et al. (1994), "Enhancement of Mucosal IgA Responses by Interleukins 5 and 6 Encoded in Recombinant Vaccine Vectors." *Reproduction, Fertility, and Development*, vol. 6(3):389–392.

Robinson et al. (1993), "Use of Direct DNA Inoculations to Elicit Protective Immune Responses." *Journal of Cellular Biochemistry, Supplement* 17D:85, 92.

Sano et al. (1989), "Binding Propeties of Human Anti–DNA Antibodies to Cloned Human DNA Fragments." *Scand. J. Immunol.*, vol. 30:51–63.

Schleimer et al. (1992), "IL–4 Induced Adherence of Human Eosinophils and Basophils but not Neutrophils to Endothelium." *The Journal of Immunology*, vol. 148(4):1086–1092.

Secrist et al. (1993), "Allergen Immunotherapy Decreases Interleukin 4 Production in CD4+ T Cells from Allergic Individuals." *J. Exp. Med.*, vol. 178:2123–2130.

Sparwasser et al. (1997), "Bacterial DNA causes septic shock." *Nature*, vol. 386(6623):336–337.

Spier (1996), "International Meeting on the Nucleic Acid Vaccines for the Prevention of Infectious Diseases and Regulating Nucleic Acid (DNA) vaccines." *Vaccine*, vol. 14(13):1258–1288.

Tam et al. (1997), "Oligonucleotide–Mediated Inhibition of CD28 Expression Induces Human T Cell Hyporesponsiveness and Manifests Impaired Contact Hypersensitivity in Mice." *The Journal of Immunology*, vol. 158(1):200–208.

Tanaka et al. (1992), "An Antisense Oligonucleotide Complementary to a Sequence in l$\gamma$2b Increases $\gamma$2b Germline Transcripts, Stimulates B Cell DNA Synthesis, and Inhibits Immunoglobulin Secretion." *The Journal of Experimental Medicine*, vol. 175:597–607.

Terr, "Allergy Desensitization." Chapter 56:739–743.

Ulmer et al. (1993), "Heterologous protection Against Influenza by Injection of DNA Encoding a Viral Protein." *Science*, vol. 259:1745–1748.

Warren (1998), "Adjuvants." *Encyclopedia of Immunology, $2^{nd}$ Edition*, vol. 1.

Yakubov et al. (1989), "Mechanism of oligonucleotide uptake by cells: Involvement of specific receptors?" *Proc. Natl. Acad. Sci.*, vol. 86:6454–6458.

Yamamoto (1994), "Mode of Action of Oligonucleotide Fraction Extracted From *Mycobacterium bovis* BCG." *Kekkaku*, vol. 69(9):29–32.

Zhao et al. (1993), "Comparison of Cellular Binding and Uptake of Antisense Phosphodiester, Phosphorothioate, and Mixed Phosphorothioate and Methylphosphonate Oligonucleotides." *Antisense Research and Development*, vol. 3:53–66.

Multi–Test:product insert (1984) *Lincoln Diagnostics*, Inc.

Raz, et al., "Potential Role of Immunostimulatory DNA Sequences (ISS) in Genetic Immunization and Autoimmunity," *Cytokines and Inflammatory Mediators*, ACR Poster Session C, Oct. 20, 1996.

* cited by examiner

SEQUENCE LISTING

```
<160> NUMBER OF SEQ ID NOS: 20

<210> SEQ ID NO 1
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 1 aacgtt                                                                    6

<210> SEQ ID NO 2
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 2 agcgtc                                                                    6

<210> SEQ ID NO 3
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 3 gacgtt                                                                    6

<210> SEQ ID NO 4
```

```
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 4 ggcgtt                                                                 6

<210> SEQ ID NO 5
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 5 aacgtc                                                                 6

<210> SEQ ID NO 6
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 6 agcgtc                                                                 6

<210> SEQ ID NO 7
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 7 gacgtc                                                                 6

<210> SEQ ID NO 8
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 8 ggcgtc                                                                 6

<210> SEQ ID NO 9
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 9 aacgcc                                                                 6

<210> SEQ ID NO 10
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 10
``` agcgcc                                                              6

<210> SEQ ID NO 11
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 11 gacgcc                                                              6

<210> SEQ ID NO 12
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 12 ggcgcc                                                              6

<210> SEQ ID NO 13
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 13 agcgct                                                              6

<210> SEQ ID NO 14
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 14 gacgct                                                              6

<210> SEQ ID NO 15
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 15 ggcgct                                                              6

<210> SEQ ID NO 16
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 16 ttcgaa                                                              6

<210> SEQ ID NO 17
<211> LENGTH: 6
<212> TYPE: DNA

```
<213> ORGANISM: Artificial Sequence
<220> FEATURE:
<223> OTHER INFORMATION: Recombinant or Synthetic Sequence

<400> SEQUENCE: 17 ggcgtt                                                                          6

<210> SEQ ID NO 18
<211> LENGTH: 6
<212> TYPE: DNA
<213> ORGANISM: Artificial Sequence
<220> FEATURE:
<223> OTHER INFORMATION: Recombinant or Synthetic Sequence

<400> SEQUENCE: 18 aacgcc                                                                          6

<210> SEQ ID NO 19
<211> LENGTH: 22
<212> TYPE: DNA
<213> ORGANISM: Artificial Sequence
<220> FEATURE:
<223> OTHER INFORMATION: Recombinant or Synthetic Sequence

<400> SEQUENCE: 19
tgactgtgaa cgttcgagat ga                                                       22

<210> SEQ ID NO 20
<211> LENGTH: 22
<212> TYPE: DNA
<213> ORGANISM: Artificial Sequence
<220> FEATURE:
<223> OTHER INFORMATION: Recombinant or Synthetic Sequence

<400> SEQUENCE: 20
tgactgtgaa ggttggagat ga                                                       22
```

IMMUNIZATION-FREE METHODS FOR TREATING ANTIGEN-STIMULATED INFLAMMATION IN A MAMMALIAN HOST AND SHIFTING THE HOST'S ANTIGEN IMMUNE RESPONSIVENESS TO A TH1 PHENOTYPE

CROSS-REFERENCE

This application is a continuation of U.S. patent application Ser. No. 08/927,120, filed Sep. 5, 1997, now abandoned, which application is incorporated by reference herein, and to which application I claim priority.

STATEMENT OF GOVERNMENT RIGHTS

This invention was made with Government support under Grant No. AI37305, awarded by the National Institutes of Health. The Government may have certain rights in this invention.

FIELD OF THE INVENTION

The invention relates to methods and oligonucleotide compositions for use in reducing or suppressing granulocyte-mediated inflammation in a host tissue and in modulating the host's immune responsiveness to an antigen.

HISTORY OF THE RELATED ART

In vertebrates, endothelial cell adhesion by granulocytes (eosinophils, basophils, neutrophils and mast cells) is followed by the release of inflammatory mediators, such as leukotrienes, major basic protein and histamine. In susceptible individuals, the resulting inflammation can damage affected host tissues.

The most common pathologic inflammatory condition is asthma, which is characterized by marked eosinophil infiltration into respiratory airways, followed by inflammation-induced tissue damage. Other pathologic inflammatory conditions associated with granulocyte infiltration into affected tissues include nasal polyposis, allergic rhinitis, allergic conjunctivitis, atopic dermatitis, eosinophilic fasciitis, idiopathic h y pereosinbphilic syndrome and cutaneous basophil hypersensitivity, as well as inflammation and fibrosis resulting from increased production of granulocytestimulatory cytokines, such as interleukin (IL)-5 and certain interferons (1NF).

Routine treatment of such conditions is typically directed toward inhibiting the activity of inflammatory mediators released after granulocyte adhesion to endothelia (e.g., by delivering a corticoid composition to the affected tissues). Where the identity of an inflammation inducing antigen is known, some immune protection against further antigen challenge can be provided through immunization. However, although effective in stimulating production of neutralizing antibodies, canonical immunization does not effectively stimulate longer term cellular immunity. Moreover, antigen immunization stimulates host production of IL-4 and IL-5. IL-5 encourages granulocyte adhesion to endothelia while IL-4 induces immunoglobulin switching to the IgE isotype at the risk of anaphylaxis.

SUMMARY OF THE INVENTION

The invention provides means to rapidly suppress antigen-stimulated inflammation in a mammalian host by suppressing granulocyte infiltration into a host tissue. The invention also provides immunization-free means to provide protection to an antigen-sensitized mammalian host against subsequent antigen challenge without risk of anaphylaxis. These aims are achieved by the invention through delivery of an immunostimulatory oligonucleotide (ISS-ODN) to the host without codelivery of an immunizing antigen.

Surprisingly, ISS-ODN have anti-inflammatory properties in addition to their immunostimulatory properties. ISSODN are therefore useful in the treatment and prevention of inflammation associated with antigen-stimulated granulocyte infiltration of tissue, such as occurs in the respiratory passages of asthmatics during an asthma attack. Advantageously, delivery of ISS-ODN according to the invention suppresses antigen-stimulated granulocyte infiltration into host tissue even before the ISS-ODN affect the host's immune response to the antigen. Thus, the invention provides an antigen-independent method to reduce antigen-stimulated inflammation by suppressing cellular adhesion, thereby avoiding the release of inflammatory mediators which would be stimulated through granulocyte-binding of endothelial cells.

An example of a therapeutic application for the invention is in the control of asthma, whereby the ISS-ODN are delivered into pulmonary tissue intranasally or by systemic routes. In asthmatics, eosinophil infiltration of lung tissue occurs mainly during the late phase of an allergic response to a respiratory allergen. Canonical immunotherapy can modulate the host immune response to the allergen and eventually stem the tide of eosinophils into the host airways. However, practice of the invention suppresses eosinophil infiltration of host airways well before the host immune system responds to the respiratory allergen, thereby providing a form of protection against the airway narrowing and respiratory tissue damage which characterize an acute asthma attack.

In another aspect, the invention provides means to shift a present host cellular immune response to an antigen away from a Th2 phenotype and into a Th1 phenotype. To this end, ISS-ODN are delivered by any route through which antigen-sensitized host tissues will be contacted with the ISSODN. ISS-ODN administered in this fashion boost both humoral (antibody) and cellular (Th1 type) immune responses of the host. Unlike canonical immunotherapy, immunity is stimulated by this method of the invention even when no additional antigen is introduced into the host. Thus, use of the method to boost the immune responsiveness of a host to subsequent challenge by a sensitizing antigen without immunization avoids the risk of immunization-induced anaphylaxis, suppresses IgE production in response to the antigen challenge and eliminates the need to identify the sensitizing antigen for use in immunization. An especially advantageous use for this aspect of the invention is treatment of localized allergic responses in target tissues where the allergens enter the body, such as the skin and mucosa.

Suppression of the Th2 phenotype according to the invention is also a useful adjunct to canonical immunotherapy to reduce antigenstimulated IL-4 and IL-5 production. Thus, the invention encompasses delivery of ISS-ODN to a host to suppress the Th2 phenotype associated with conventional antigen immunization (e.g., for vaccination or allergy immunotherapy).

The shift to a Th1 phenotype achieved according to the invention is accompanied by increased secretion of IFN a, P and y, as well as IL-12 and IL-18. Each of these cytokines enhance the host's immune defenses against intracellular pathogens, such as viruses. Thus, the invention encompasses delivery of ISS-ODN to a host to combat pathogenic infection.

Angiogenesis is also enhanced in the Th1 phenotype (ostensibly through stimulation by IL-12). Thus, the invention encompasses delivery of ISS-ODN to a host to stimulate therapeutic angiogenesis to treat conditions in which localized blood flow plays a significant etiological role, such as in diabetic retinopathy.

Pharmaceutically acceptable compositions of ISS-ODN are provided for use in practicing the methods of the invention. The ISS-ODN of the invention include DNA or RNA oligonucleotides which are enriched with CpG dinucleotides, including those which are comprised of the primary structure 5'-Purine-Purine-[C]-[G]-Pyrimidine-Pyrimidine-3'.

Where appropriate to the contemplated course of therapy, the ISS-ODN may be administered with other anti-inflammatory or immunotherapeutic agents. Thus, a particularly useful composition for use in practicing the method of the invention is one in which an anti-inflammatory agent (e.g., a glucocorticoid) or immunotherapeutic agent (e.g., an antigen, cytokine or adjuvant) is mixed with, or conjugated to, an ISS-ODN.

The ISS-ODN can also be provided in the form of a kit comprising ISS-ODN and any additional medicaments, as well as a device for delivery of the ISS-ODN to a host tissue and reagents for determining the biological effect of the ISS-ODN on the treated host.

DETAILED DESCRIPTION OF THE INVENTION

A. Anti-Inflammatory and Immunotherapeutic Methods of the Invention

1. Therapeutic Effects of the Methods of the Invention

Figure 1:
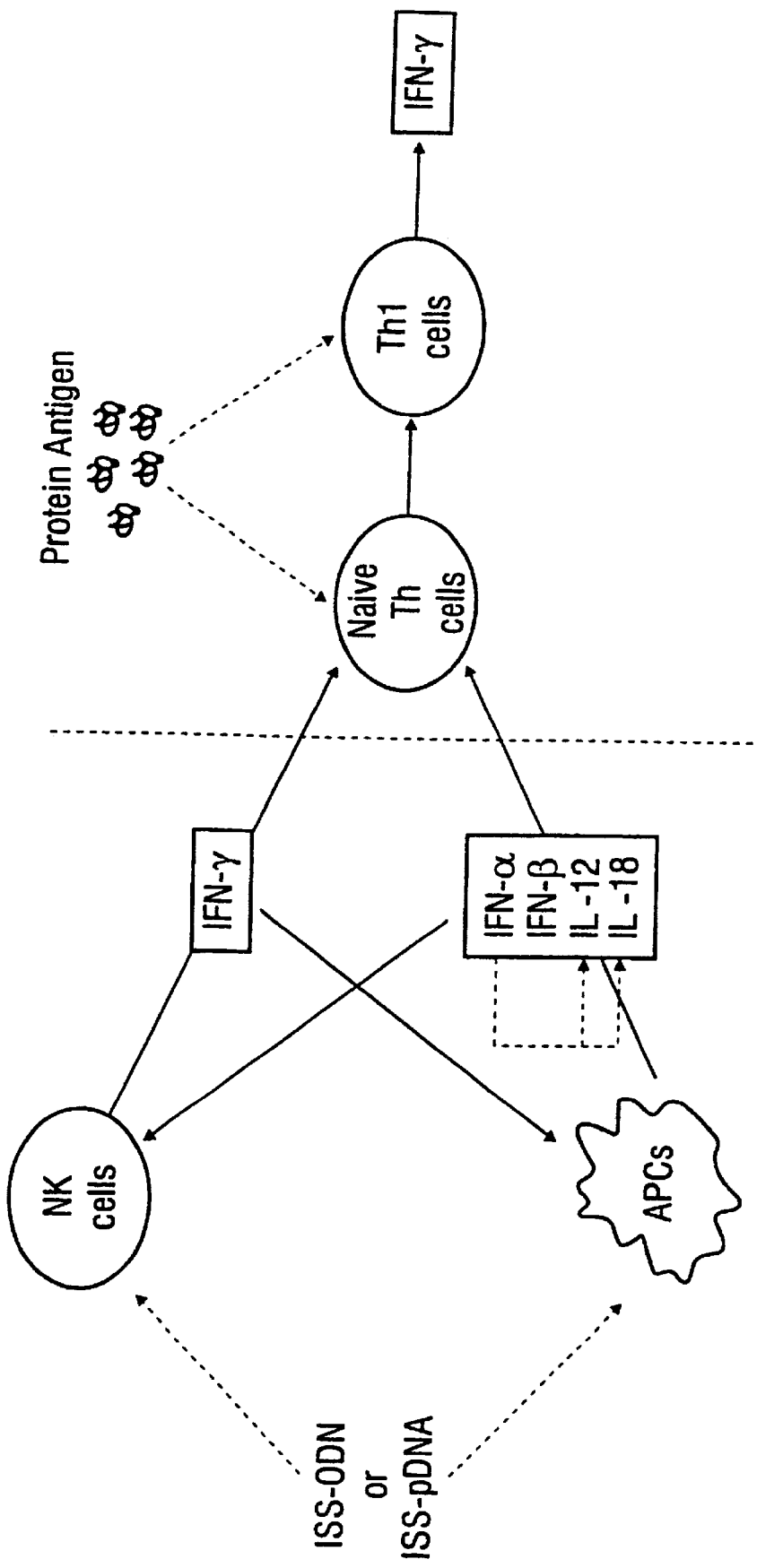
FIG. 1 is a chart which summarizes aspects of the mammalian immune system.

The main therapeutic goals which may be achieved through practice of the methods of the invention are treatment of inflammation and boosting of host immune responsiveness with a Th1 phenotype against a sensitizing antigen. Both goals are achieved by delivering ISSODN to an antigensensitized host; i.e., a mammal whose immune system has been primed to respond to challenge by a sensitizing antigen. For purposes of this disclosure, "sensitizing antigen" refers to an exogenous, immunogenic protein, peptide, glycoprotein, lipid or polysaccharide. For reference, a chart summarizing aspects of mammal antigen immunity is appended as FIG. 1.

The anti-inflammatory method of the invention is useful in suppressing the onset of, and in reducing, acute granulocyte-mediated inflammation in an antigen-sensitized host. Specifically, treatment of an antigen-sensitized (primed) host before subsequent antigen challenge suppresses antigenstimulated infiltration of host tissue by granulocytes (especially, eosinophils and basophils). Similarly, treatment of an antigen-sensitized host on or after antigen challenge reduces antigenstimulated infiltration of host tissue by granulocytes. Advantageously, the anti-inflammatory impact of ISS-ODN delivered according to the invention is rapid, taking effect even before the ISSODN would be expected to impact the host's immune responsiveness to the sensitizing antigen. The invention therefore provides the host with fairly immediate protection against tissue damage from granulocyte-mediated inflammation.

For example, as shown by the data in Example II, antigen-sensitized animal models of allergic asthma treated with ISS-ODN without concurrent antigen challenge experienced as much as a 90% reduction of eosinophil infiltration into respiratory tissue as compared to control animals and animals treated only with an inactive ISS-ODN mutant. Significantly, reduction of eosinophil infiltration in previously challenged mice, or suppression of eosinophil infiltration in primed, unchallenged mice, was obtained within as little as 24 hours of delivery of the ISS-ODN. The effect of the ISS-ODN on eosinophil infiltration is therefore independent of the later-developing host immune response to the sensitizing antigen. Being antigen independent, the ISS-ODN can be utilized as inflammation suppressors before antigen challenge or during a period when the risk of antigen challenge is present (e.g., during an allergy season). Importantly, as shown in Examples IV and VI, IS SODN can be used according to the invention to prevent inflammation or an immune response on subsequent antigen challenge in an antigen-primed host as well as to reduce inflammation or other antigenstimulated immune responses after antigen challenge.

Although the invention is not limited to any mechanism of action, it is probable that the antiinflammatory activity of ISS-ODN is at least in part a consequence of IL-5 suppression. However, suppression of granulocyte accumulation in host tissue is achieved more rapidly (within 24 hours) than immune activation of cytokine-secreting lymphocytes would be expected to occur. It is therefore also possible that ISSODN administered according to the invention physically interfere with granulocyte adhesion to endothelial, perhaps by blocking VCAM-1 endothelial receptors, their eosinophilic ligand (VLA-4) or by lysing granulocytes. Whatever the mechanism, ISS-ODN suppression of granulocyte accumulation according to the invention appears to be independent of ISS-ODN stimulation of the host immune system.

The immunotherapeutic method of the invention produces a vaccination-like immune response to challenge by a sensitizing antigen without concurrent exposure of the host to the antigen. Immune stimulation achieved through practice of the invention is comparable to the immune stimulation which occurs on vaccination of a host with a sensitizing antigen. Thus, the methods of the invention provides means to immunize a host against a sensitizing antigen without deliberate antigen challenge.

Advantageously, the immune response stimulated according to the invention differs from an immunization response in that the latter develops in a Th2 phenotype while the former develops in a Th1 phenotype. In this regard, it is helpful to recall that CD4+ lymphocytes generally fall into one of two distinct subsets; i.e., the Th1 and Th2 cells. Th1 cells principally secrete IL-2, IFNy and TNFP (the latter two of which mediate macrophage activation and delayed type hypersensitivity) while Th2 cells principally secrete IL-4 (which stimulates production of IgE antibodies), IL-5 (which stimulates granulocyte infiltration of tissue), IL-6 and IL-10. These CD4+ subsets exert a negative influence on one another; i.e., secretion of Th1 lymphokines inhibits secretion of Th2 lymphokines and vice versa.

Factors believed to favor Th1 activation resemble those induced by viral infection and include intracellular pathogens, exposure to IFNP, IFN-a, IFNγ, IL-12 and IL-18 and exposure to low doses of antigen. Th1 type immune responses also predominate in autoimmune disease. Factors believed to favor Th2 activation include exposure to IL-4 and IL-10, APC activity on the part of B lymphocytes and high doses of antigen. Active Th1 (IFNγ) cells enhance cellular immunity and are therefore of particular value in responding to intracellular infections, while active Th2 cells enhance antibody production and are therefore of value in responding to extracellular infections (at the risk of anaphylactic events associated with IL-4 stimulated induction of IgE antibody production). Thus, the ability to shift host immune responses from the Th1 to the Th2 repertoire and vice versa has substantial clinical significance for controlling host immunity against antigen challenge (e.g., in infectious and allergic conditions).

To that end, the methods of the invention shift the host immune response to a sensitizing antigen toward a Th1 phenotype (Example IV). Consequently, antigen-stimulated/Th2 associated IL-4, IL-5 and IL-10 secretion (Example VI), IL-5 stimulated granulocyte infiltration of antigen-sensitized tissue (Examples II and III) and IL-4 stimulated production of IgE (Example V) are suppressed, thereby reducing the host's risk of prolonged allergic inflammation and minimizing the risk of antigen-induced anaphylaxis. Although the invention is not limited to any particular mechanism of action, it is conceivable that ISS-ODN facilitate uptake of exogenous antigen by antigen presenting cells for presentation through host MHC Class I processing pathways. Whatever the mechanism of action, use of ISS-ODN to boost the host's immune responsiveness to a sensitizing antigen and shift the immune response toward a Th1 phenotype avoids the risk of immunization-induced anaphylaxis, suppresses IgE production in response to a sensitizing antigen and eliminates the need to identify the sensitizing antigen for use in immunization.

With reference to the invention, ISS-ODN mediated "reduction of inflammation" (in a primed, antigen-challenged host), "prevention of inflammation" (in a primed host before antigen challenge) and "boosting of immune responsiveness in a Th1 phenotype" in an ISS-ODN treated host are evidenced by any of the following events:

(1) a reduction in levels of IL-4 measured before and after antigen-challenge; or detection of lower (or even absent) levels of IL-4 in a treated host as compared to an antigenprimed, or primed and challenged, control;

(2) an increase in levels of IL-12, IL- 18 and/or IFN (α, β or γ) before and after antigen challenge; or detection of higher levels of IL12, IL-18 and/or IFN (α, β or γ) in an IS SODN treated host as compared to an antigen-primed or, primed and challenged, control;

(3) IgG2a antibody production in a treated host; or (4) a reduction in levels of antigen-specific IgE as measured before and after antigen challenge; or detection of lower (or even absent) levels of antigen-specific IgE in an ISSODN treated host as compared to an antigen-primed, or primed and challenged, control.

Also, with respect to reduction and prevention of inflammation in particular, an especially meaningful indicia of the efficacy of the inventive method in a treated host is:

(5) a reduction in granulocyte counts (e.g., of eosinophils or basophils, depending on which cell type is most involved in the condition affecting the host) in inflammatory infiltrate of an affected host tissue as measured in an antigen-challenged host before and after ISSODN administration, or detection of lower (or even absent) levels of eosinophil or basophil counts in a treated host as compared to an antigen-primed, or primed and challenged, control.

Exemplary methods for determining such values are described further in the Examples.

2. Methods and Routes for Administration of ISS-ODN to a Host

The ISS-ODN of the invention are administered to a host using any available method and route suitable for drug delivery, including ex vivo methods (e.g., delivery of cells incubated or transfected with an ISS-ODN) as well as systemic or localized routes. However, those of ordinary skill in the art will appreciate that methods and localized routes which direct the ISS-ODN into antigensensitized tissue will be preferred in most circumstances to systemic routes of administration, both for immediacy of therapeutic effect and avoidance of oligonucleotide degradation in vivo.

The entrance point for many exogenous antigens into a host is through the skin or mucosa. Thus, delivery methods and routes which target the skin (e.g., for cutaneous and subcutaneous conditions) or mucosa (e.g., for respiratory, ocular, lingual or genital conditions) will be especially useful. Those of ordinary skill in the clinical arts will be familiar with, or can readily ascertain, means for drug delivery into skin and mucosa. For review, however, exemplary methods and routes of drug delivery useful in the invention are briefly discussed below.

Intranasal administration means are particularly useful in addressing respiratory inflammation, particularly inflammation mediated by antigens transmitted from the nasal passages into the trachea or bronchioli. Such means include inhalation of aerosol suspensions or insufflation of the polynucleotide compositions of the invention. Nebulizer devices suitable for delivery of polynucleotide compositions to the nasal mucosa, trachea and bronchioli are well-known in the art and will therefore not be described in detail here. For general review in regard to intranasal drug delivery, those of ordinary skill in the art may wish to consult Chien, *Novel Drug Delivery Systems*, Ch. S (Marcel Dekker, 1992).

Dermal routes of administration, as well as subcutaneous injections, are useful in addressing allergic reactions and inflammation in the skin. Examples of means for delivering drugs to the skin are topical application of a suitable pharmaceutical preparation, transdermal transmission, injection and epidermal administration.

For transdermal transmission, absorption promoters or iontophoresis are suitable methods. For review regarding such methods, those of ordinary skill in the art may wish to consult Chien, supra at Ch. 7. Iontophoretic transmission may be accomplished using commercially available "patches" which deliver their product continuously via electric pulses through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or to dose periodically. Preparation and use of the patch should be performed according to the manufacturer's printed instructions which accompany the LECTRO PATCH product; those instructions are incorporated herein by this reference.

Epidermal administration essentially involves mechanically or chemically irritating the outermost layer of the epidermis sufficiently to provoke an immune response to the irritant. An exemplary device for use in epidermal administration employs a multiplicity of very narrow diameter, short tynes which can be used to scratch ISS-ODN coated onto the tynes into the skin. The device included in the MONO-VACC old tuberculin test manufactured by Pasteur Merieux of Lyon, France is suitable for use in epidermal administration of ISS-ODN. Use of the device is according to the manufacturer's written instructions included with the device product; these instructions regarding use and administration are incorporated herein by this reference to illustrate conventional use of the device. Similar devices which may also be used in this embodiment are those which are currently used to perform allergy tests.

Ophthalmic administration (e.g., for treatment of allergic conjunctivitis) involves invasive or topical application of a pharmaceutical preparation to the eye. Eye drops, topical cremes and injectable liquids are all examples of suitable mileaus for delivering drugs to the eye.

Systemic administration involves invasive or systemically absorbed topical administration of pharmaceutical preparations. Topical applications as well as intravenous and intramuscular injections are examples of common means for systemic administration of drugs.

3. Dosing Parameters for ISS-ODN

A particular advantage of the ISS-ODN of the invention is their capacity to exert anti-inflammatory and immunotherapeutic activity even at relatively minute dosages. Although the dosage used will vary depending on the clinical goals to be achieved, a suitable dosage range is one which provides up to about 1–1000, ug of ISS-ODN/ml of carrier in a single dosage. In view of the teaching provided by this disclosure, those of ordinary skill in the clinical arts will be familiar with, or can readily ascertain, suitable parameters for administration of ISS-ODN according to the invention.

In this respect, it should be noted that the anti-inflammatory and immunotherapeutic activity of ISSODN in the invention is essentially dose-dependent. Therefore, to increase ISS-ODN potency by a magnitude of two, each single dose is doubled in concentration. Clinically, it may be advisable to administer the ISS-ODN in a low dosage (e.g., about 1 Pg/ml to about 50~tg/ml), then increase the dosage as needed to achieve the desired therapeutic goal. Alternatively, a target dosage of ISSODN can be considered to be about 1–10 gM in a sample of host blood drawn within the first 24–48 i hours after administration of ISS-ODN. Based on current studies, ISS-ODN are believed to have little or no toxicity at these dosage levels.

B. ISS-ODN Anti-inflammatory Compositions

1. ISS-ODN Structure

Functionally, ISS-ODN enhance the cellular and humoral immune responses in a host, particularly lymphocyte proliferation and the release of cytokines (including IFN) by host monocytes and natural killer (NK) cells. Immunostimulation by synthetic ISS-ODN in vivo occurs by contacting host lymphocytes with, for example, ISS-ODN oligonucleotides, ISS-ODN oligonucleotideconjugates and ISS-containing recombinant expression vectors (data regarding the activity of ISSODN conjugates and ISS-ODN vectors are set forth in co-pending, commonly assigned U.S. patent applications Ser. No. 60/028,118, filed Oct. 11, 1996, and Ser. No. 08/593,554, filed Jan. 30, 1996, now abandoned; data from which is incorporated herein by reference to demonstrate ISS-ODN immunostimulatory activity in vivo). Thus, while native microbial ISS-ODN stimulate the host immune system to respond to infection, synthetic analogs of these ISS-ODN are useful therapeutically to modulate the host immune response not only to microbial antigens, but also to tumor antigens, allergens and other substances.

Structurally, ISS-ODN are non-coding oligonucleotides 6 mer or greater in length which may include at least one unmethylated CpG motif. The relative position of each CpG sequence in ISSODN with immunostimulatory activity in certain mammalian species (e.g., rodents) is 5'-CG-3' (i.e., the C is in the 5' position with respect to the G in the 3' position). Many known ISS-ODN flank the CpG motif with at least two purine nucleotides (e.g., GA or AA) and at least two pyrimidine nucleotides (5'-Purine-Purine[C]-[G]-Pyrimidine-Pyrimidine-3'). CpG motif-containing ISS-ODN are believed to stimulate B lymphocyte proliferation see, e.g., Krieg, et al., *Nature*, 374:546–549, 1995).

The core hexamer structure of the foregoing IS S-ODN may be flanked upstream and/or downstream by any number or composition of nucleotides or nucleosides. However, ISS-ODN are at least 6 mer in length, and preferably are between 6 and 200 mer in length, to enhance uptake of the ISS-ODN into target tissues. Those of ordinary skill in the art will be familiar with, or can readily identify, reported nucleotide sequences of known ISS-ODN. For ease of reference in this regard, the following sources are especially helpful:

Yamamoto, et al., *Microbiol.ImmunoL,* 36:983 (1992)
Ballas, et al., *JImmunoL,* 157:1840 (1996)
Klinman, et al., *JImmunoL,* 158:3635 (1997)
Sato, et al., *Science,* 273:352 (1996)

Each of these articles are incorporated herein by reference for the purpose of illustrating the level of knowledge in the art concerning the nucleotide composition of IS S-ODN.

In particular, ISS-ODN useful in the invention include those which have the following hexameric nucleotide sequences:

1. ISS-ODN having "CpG" dinucleotides; and,
2. Inosine and/or uracil substitutions for nucleotides in the foregoing hexamer sequences for use as RNA IS S-ODN.

For example, DNA based ISS-ODN useful in the invention include those which have the following hexameric nucleotide sequences:

AACGTT, AGCGTC, GACGTT, GGCGTT, AACGTC, AGCGTC, GACGTC, GGCGTC, AACGCC, AGCGCC, GACGCC, GGCGCC, AGCGCT, GACGCT, GGCGCT, TTCGAA, GGCGTT and AACGCC   (respectively, SEQ.ID.Nos. 1–18).

ISS-ODN may be single-stranded or double-stranded DNA, single or double-stranded RNA and/or oligonucleosides. The ISS-ODN may or may not include palindromic regions. If present, a palindrome may extend only to a CpG motif, if present, in the core hexamer sequence, or may encompass more of the hexamer sequence as well as flanking nucleotide sequences.

The nucleotide bases of the ISS-ODN which flank the CpG motif of the core hexamer and/or make up the flanking nucleotide sequences may be any known naturally occurring bases or synthetic nonnatural bases (e.g., TCAG or, in RNA, UACGI). Oligonucleosides may be incorporated into the internal region and/or termini of the ISS-ODN using conventional techniques for use as attachment points for other compounds (e.g., peptides). The base(s), sugar moiety, phosphate groups and termini of the ISS-ODN may also be modified in any manner known to those of ordinary skill in the art to construct an ISS-ODN having properties desired in addition to the described activity of the ISSODN. For example, sugar moieties may be attached to nucleotide bases of ISS-ODN in any steric configuration.

In addition, backbone phosphate group modifications (e.g., methylphosphonate, phosphorothioate, phosphoroamidate and phosphorodithioate internucleotide linkages) can confer anti-microbial activity on the ISS-ODN and enhance their stability in vivo, making them particularly useful in therapeutic applications. A particularly useful phosphate group modification is the conversion to the phosphorothioate or phosphorodithioate forms of the ISS-ODN oligonucleotides. In addition to their potentially anti-microbial properties, phosphorothioates and phosphorodithioates are more resistant to degradation in vivo than their unmodified oligonucleotide counterparts, making the ISS-ODN of the invention more available to the host.

2. Synthesis of, and Screening for, ISS-ODN

ISS-ODN can be synthesized using techniques and nucleic acid synthesis equipment which are wellknown in the art. For reference in this regard, see, e.g., Ausubel, et al., *Current Protocols in Molecular Biology*, Chs. 2 and 4 (Wiley Interscience, 1989); Maniatis, et al., *Molecular Cloning: A Laboratory Manual* (Cold Spring Harbor Lab., New York, 1982); U.S. Pat. Nos. 4,458,066 and 4,650,675. These references are incorporated herein by reference for the sole purpose of demonstrating knowledge in the art concerning production of synthetic oligonucleotides. Because the ISS-ODN is non-coding, there is no concern about maintaining an open reading frame during synthesis.

ISS-ODN may be incorporated into a delivery vector, such as a plasmid, cosmid, virus or retrovirus, which may in turn code for therapeutically beneficial polypeptides, such as cytokines, hormones and antigens. Incorporation of ISS-ODN into such a vector does not adversely affect their activity.

Alternatively, ISS-ODN may be isolated from microbial species (especially mycobacteria) using techniques wellknown in the art, such as nucleic acid hybridization. Preferably, such isolated ISSODN will be purified to a substantially pure state; i.e., to be free of endogenous contaminants, such as lipopolysaccharides. ISS-ODN isolated as part of a larger polynucleotide can be reduced to the desired length by techniques well known in the art, such as by endonuclease digestion. Those of ordinary skill in the art will be familiar with, or can readily ascertain, techniques suitable for isolation, purification and digestion of polynucleotides to obtain ISS-ODN of potential use in the invention.

Confirmation that a particular oligonucleotide has the properties of an ISS-ODN useful in the invention can be obtained by evaluating whether the ISS-ODN affects cytokine secretion and IgG antibody isotype production as described in Section A.I, above. Details of in vitro techniques useful in making such an evaluation are given in the Examples; those of ordinary skill in the art will also know of, or can readily ascertain, other methods for measuring cytokine secretion and antibody production along the parameters taught herein.

The techniques for making phosphate group modifications to oligonucleotides are known in the art and do not require detailed explanation. For review of one such useful technique, the an intermediate phosphate triester for the target oligonucleotide product is prepared and oxidized to the naturally occurring phosphate triester with aqueous iodine or with other agents, such as anhydrous amines. The resulting oligonucleotide phosphoramidates can be treated with sulfur to yield phophorothioates. The same general technique (excepting the sulfur treatment step) can be applied to yield methylphosphoamidites from methylphosphonates. For more details concerning phosphate group modification techniques, those of ordinary skill in the art may wish to consult U.S. Pat. Nos. 4,425,732; 4,458,066; 5,218,103 and 5,453,496, as well as *Tetrahedron Lett.* at 21:4149 (1995), 7:5575 (1986), 25:1437 (1984) and *Journal Am. ChemSoc.*, 93:6657 (1987), the disclosures of which are incorporated herein for the sole purpose of illustrating the standard level of knowledge in the art concerning preparation of these compounds.

A colloidal dispersion system may be used for targeted delivery of the ISS-ODN to an inflamed tissue. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome.

Liposomes are artificial membrane vesicles which are useful as delivery vehicles in vitro and in vivo. It has been shown that large unilamellar vesicles (LUV), which range in size from 0.2–4.0, um can encapsulate a substantial percentage of an aqueous buffer containing large macromolecules. RNA, DNA and intact virions can be encapsulated within the aqueous interior and be delivered to cells in a biologically active form (Fraley, et al, *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) ,encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phasetransitiontemperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cellspecific, and organellespecific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various well known linking groups can be used for joining the lipid chains to the targeting ligand (see, e.g., Yanagawa, et al., *Nuc.Acids Symp.Ser.,* 19:189 (1988); Grabarek, et al., *AnaLBiochem.,* 185:131 (1990); Staros, et al., *Anal.Biochem.,* 156:220 (1986) and Boujrad, et al., *Proc.Natl.Acad Sci. USA,* 90:5728 (1993), the disclosures of which are incorporated herein by reference solely to illustrate the standard level of knowledge in the art concerning conjugation of oligonucleotides to lipids). Targeted delivery of ISS-ODN can also be achieved by conjugation of the ISS-ODN to a surface of viral and non-viral recombinant expression vectors, to an antigen or other ligand, to a monoclonal antibody or to any molecule which has the desired binding specificity.

Examples of other useful conjugate partners include any immunogenic antigen (including allergens, live and attenuated viral particles and tumor antigens), targeting peptides (such as receptor ligands, antibodies and antibody fragments, hormones and enzymes), non-peptidic antigens (coupled via a peptide linkage, such as lipids, polysaccharides, glycoproteins, gangliosides and the like) and cytokines (including interleukins, interferons, erythropoietin, tumor necrosis factor and colony stimulating factors). Such conjugate partners can be prepared according to conventional techniques (e.g., peptide synthesis) and many are commercially available.

Those of ordinary skill in the art will also be familiar with, or can readily determine, methods useful in preparing oligonucleotide-peptide conjugates. Conjugation can be accomplished at either termini of the ISS-ODN or at a suitably modified base in an internal position (e.g., a cytosine or uracil). For reference, methods for conjugating oligonucleotides to proteins and to oligosaccharide moieties of Ig are known (see, e.g., O'Shannessy, et al., *J.Applied Biochem.,* 7:347 (1985), the disclosure of which is incorporated herein by reference solely to illustrate the standard level of knowledge in the art concerning oligonucleotide conjugation). Another useful reference is Kessler: "Nonradioactive Labeling Methods for Nucleic Acids", in Kricka (ed.), *Nonisotopic DNA Probe Techniques* (Acad.Press, 1992)).

Briefly, examples of known, suitable conjugation methods include: conjugation through 3' attachment via solid support chemistry see, e.g., Haralambidis, et al., *Nuc.Acids Res.,* 18:493 (1990) and Haralambidis, et al., *Nuc.Acids Res.,* 18:501 (1990) [solid support synthesis of peptide partner]; Zuckermann, et al., *Nuc.Acids Res.,* 15:5305 (1987), Corey, et al., *Science,* 238:1401 (1987) and Nelson, et al., *Nuc. Acids Res.,* 17:1781 (1989) [solid support synthesis of oligonucleotide partner]).

Amino-amino group linkages may be performed as described in Benoit, et al., *Neuromethods,* 6:43 (1987), while thiol-carboxyl group linkages may be performed as described in Sinah, et al., *Oligonucleotide Analogues:A Practical Approach* (IRL Press, 1991). In these latter methods, the oligonucleotide partner is synthesized on a solid support and a linking group comprising a protected amine, thiol or carboxyl group opposite a phosphoramidite is covalently attached to the 5'-hydroxyl see, e.g., U.S. Pat. Nos. 4,849,513; 5,015,733; 5,118,800 and 5,118,802).

Linkage of the oligonucleotide partner to a peptide may also be made via incorporation of a linker arm (e.g., amine or carboxyl group) to a modified cytosine or uracil base see, e.g., Ruth, *4th Annual Congress for Recombinant DNA Research* at 123). Affinity linkages (e.g., biotin-streptavidin) may also be used see, e.g., Roget, et al., *Nuc.Acids Res.,* 17:7643 (1989)).

Methods for linking oligonucleotides to lipids are also known and include synthesis of oligophospholipid conjugates see, e.g., Yanagawa, et al., *Nuc. Acids Symp.Ser.,* 19:189 (1988)), synthesis of oligo-fatty acids conjugates (see, e.g., Grabarek, et al., *Anal.Biochem.,* 185:131 (1990)) and oligo-sterol conjugates (see, e.g., Boujrad, et al., *Proc.Natl.AcadSci USA,* 90:5728 (1993)).

Each of the foregoing references is incorporated herein by reference for the sole purpose of illustrating the level of knowledge and skill in the art with respect to oligonucleotide conjugation methods.

Co-administration of a peptide drug with an ISS-ODN according to the invention may also be achieved by incorporating the ISS-ODN in cis or in trans into a recombinant expression vector (plasmid, cosmid, virus or retrovirus) which codes for any therapeutically beneficial protein deliverable by a recombinant expression vector. If incorporation of an ISS-ODN into an expression vector for use in practicing the invention is desired, such incorporation may be accomplished using conventional techniques which do not require detailed explanation to one of ordinary skill in the art. For review, however, those of ordinary skill may wish to consult Ausubel, *Current Protocols in Molecular Biology,* supra.

Briefly, construction of recombinant expression vectors (including those which do not code for any protein and are used as carriers for ISS-ODN) employs standard ligation techniques. For analysis to confirm correct sequences in vectors constructed, the ligation mixtures may be used to transform a host cell and successful transformants selected by antibiotic resistance where appropriate. Vectors from the transformants are prepared, analyzed by restriction and/or sequenced by, for example, the method of Messing, et al., (*Nucleic Acids Res.,* 9:309, 1981), the method of Maxam, et al., (*Methods in Enzymology,* 65:499,1980), or other suitable methods which will be known to those skilled in the art. Size separation of cleaved fragments is performed using conventional gel electrophoresis as described, for example, by Maniatis, et al., (*Molecular Cloning,* pp. 133–134, 1982).

Host cells may be transformed with expression vectors and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

If a recombinant expression vector is utilized as a carrier for the ISS-ODN of the invention, plasmids and cosmids are particularly preferred for their lack of pathogenicity. However, plasmids and cosmids are subject to degradation in vivo more quickly than viruses and therefore may not deliver an adequate dosage of ISS-ODN to substantially inhibit ISS-ODN immunostimulatory activity exerted by a systemically administered gene therapy vector. Of the viral vector alternatives, adenoassociated viruses would possess the advantage of low pathogenicity. The relatively low capacity of adeno-associated viruses for insertion of foreign genes would pose no problem in this context due to the relatively small size in which ISS-ODN of the invention can be synthesized.

Other viral vectors that can be utilized in the invention include adenovirus, adeno-associated virus, herpes virus, vaccinia or an RNA virus such as a retrovirus. Retroviral vectors are preferably derivatives of a marine, avian or human HIV retrovirus. Examples of retroviral vectors in which a single foreign gene can be inserted include, but are not limited to: Moloney marine leukemia virus (MoMuLV), Harvey marine sarcoma virus (HaMuSV), marine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to, T2, PA317 and PA 12, for example. These cell lines produce empty virions, since no genome is packaged. If a retroviral vector is introduced into such helper cells in which the packaging signal is intact, but the structural genes are replaced by other genes of interest, the vector can be packaged and vector virion can be produced. By inserting one or more sequences of interest into the viral vector, along with another gene which encodes the ligand for a receptor on a specific target cell, for example, the vector can be rendered target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing ISSODN.

C. Pharmaceutical Compositions of ISS-ODN

If to be delivered without use of a vector or other delivery system, ISS-ODN will be prepared in a pharmaceutically acceptable composition. Pharmaceutically acceptable carriers preferred for use with the ISS-ODN of the invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. A composition of ISSODN may also be lyophilized using means well known in the art, for subsequent reconstitution and use according to the invention.

Absorption promoters, detergents and chemical irritants (e.g., keritinolytic agents) can enhance transmission of an ISS-ODN composition into a target tissue. For reference concerning general principles regarding absorption promoters and detergents which have been used with success in mucosal delivery of organic and peptide-based drugs, see Chien, *Novel Drug Delivery Systems*, Ch. 4 (Marcel Dekker, 1992).

Examples of suitable nasal absorption promoters in particular are set forth at Chien, supra at Ch. 5, Tables 2 and 3; milder agents are preferred. Suitable agents for use in the method of this invention for mucosal/nasal delivery are also described in Chang, et al., *Nasal Drug Delivery*, "Treatise on Controlled Drug Delivery", Ch. 9 and Table 3–4B thereof, (Marcel Dekker, 1992). Suitable agents which are known to enhance absorption of drugs through skin are described in Sloan, *Use of Solubility Parameters from-Regular Solution Theory to Describe Partitioning-Driven Processes*, Ch. 5, "Prodrugs: Topical and Ocular Drug Delivery" (Marcel Dekker, 1992), and at places elsewhere in the text. All of these references are incorporated herein for the sole purpose of illustrating the level of knowledge and skill in the art concerning drug delivery techniques.

D. Kits for Use in Practicing the Methods of the Invention

For use in the methods described above, kits are also provided by the invention. Such kits may include any or all of the following: ISSODN (conjugated or unconjugated); a pharmaceutically acceptable carrier (may be pre-mixed with the ISS-ODN) or suspension base for reconstituting lyophilized ISS-ODN; additional medicaments; a sterile vial for each ISS-ODN and additional medicament, or a single vial for mixtures thereof, devices) for use in delivering ISS-ODN to a host; assay reagents for detecting indicia that the antiinflammatory and/or immunostimulatory effects sought have been achieved in treated animals and a suitable assay device.

Examples illustrating the practice of the invention are set forth below. The examples are for purposes of reference only and should not be construed to limit the invention, which is defined by the appended claims. All abbreviations and terms used in the examples have their expected and ordinary meaning unless otherwise specified.

EXAMPLE I
Murine Model for the Airway Hyperreactivity of Allergic Asthma

Sensitizing-antigen challenged mice of different strains model the airway hyperreactivity seen in allergic asthma. Suitable murine strains for use in modeling the disease include Balb/c mice (which are biased genetically toward the Th2 phenotype and produce enhanced concentrations of IL-4 and IL-5 in response to antigen challenge to CD4+ lymphocytes), C57BL/6 mice (which are IL-5 deficient, for detailed study of IL-5 induced tissue damage in asthma) and W1W' mice (which are mast cell deficient, for detailed study of mast cell activation in asthma).

Disease modeling mice are conveniently prepared by intraperitoneal or subcutaneous injection of a model sensitizing antigen, ovalbumin ("OVA") in carrier (e.g., sterile saline or a carrier with adjuvant, such as alum), followed by antigen challenge with aerosolized antigen. For example, mice may be immunized with 25 gg OVA by subcutaneous injection (with or without adjuvant) weekly for 4–6 weeks, then challenged with 2 or 3 weekly aerosolizations of OVA at a concentration of 50 mg/ml in phosphate buffered saline (PBS) delivered in 20 minute intervals or at a concentration of 10 mg/ml 0.9% saline daily for about a week (in three 30 minute intervals daily). Nebulizer devices for use in the aerosolization are available from Aerotech II, CIS-US, Bedford, Mass., with a nasal chamber adapted for murine nasal passages (e.g., a nose-only chamber from Intox Products, Albuquerque, N. Mex). When driven by compressed air at a rate of 10 liters/min., the devices described produce aerosol particles having a median aerodynamic diameter of 1.4 gm.

Control mice are preferably littermates which are protein-antigen challenged without prior immunization. For further details concerning this animal model, those of skill in the art may wish to refer to Foster, et al., *JExp.Med*, 195–201, 1995; and, Corry, et al., *JExp.Med*, 109–117, 1996.

EXAMPLE II
Reduction of Eosinophil Accumulation in Lung Tissue in a Murine Asthma Model by Administration of ISS-ODN BALB/c mice, 6–10 weeks of age, were prepared as models of allergic asthma as described in Example I (subcutaneous injection of OVA followed by antigen challenge at a concentration of 50 mg OVA/ml PBS). Prior to each inhalation with OVA according to this scheme, sets of 8 mice each were treated as described in the Table below. Control mice were antigen challenged but untreated and naive mice were not challenged with antigen. All ISS doses were 100 pg per administration. Dexamethasone (a conventional steroidal anti-inflammatory used in the treatment of asthma) doses were 5 mg/kg/mouse. Priming doses of antigen were 25 [mg OVA adsorbed to alum in 0.2 ml phosphate buffered saline (PBS). Challenge doses of antigen were 1 Oml of 50 mg OVA/ml PBS. IN=intranasal; IP=intraperitoneal; SC=subcutaneous and N/A=not applicable.

| Set # | Material Received | Route and Timing |
|---|---|---|
| 1 | Naive mice (no antigen) | N/A |
| 2 | DY1018 (ISS-ODN) | IN, 1 day before the first inhalation |
| 3 | DY1018 | IN, 1 day before the second inhalation |
| 4 | DY1018 | IN, with the second inhalation |
| 5 | DY1018 | IN, 2 days after the second inhalation |
| 6 | DY1018 | IP, 1 day before the first inhalation |
| 7 | DY1018 | IP, 1 day before the second inhalation |
| 8 | DY1018 | IP, with the second inhalation |
| 9 | DY1018 | IP, 2 days after the second inhalation |
| 10 | DY1018 | IT, 2 days after the second inhalation |
| 11 | DY1019 (M-ISS-ODN) | IN, 2 days after inhalaiton |
| 12 | DY1019 | IP, 2 days after the second inhalaiton |
| 13 | DY1019 | IT, 2 days after the second inhalaiton |
| 14 | dexamethansone | SC, 2 days after the second inhalation |
| 15 | dexamethansone | SC, 7 days after the second inhalation |
| 16 | control mice (antigen only) | N/A |

DY1018 has the nucleotide sequence:

5'-TGACTGTGAACGTTCGAGATGA-3'  (SEQ.ID.No. 19)

with a phosphothioate backbone and DY1019 has the nucleotide sequence:

5'-TGACTGTGAAGGTTGGAGATGA-3'  (SEQ.ID.No. 20)

with a phosphothioate backbone.

On day 32, each mouse was bled by tail snip (approximately 501 volume) into a O.1 mM solution of PBS and EDTA. Red blood cells in solution were lysed with 1 SOmM NH4Cl and 1 OmM KHC03 in dH20 then stained (Wright-Giesma stain). Lung lavage from each mouse was obtained after sacrifice by canalization of the trachea and lavage with 800 microliters PBS, then the lavage product was stained. Bone marrow samples from each mouse were obtained by flushing of extracted femur marrow with PBS. Histological specimens of lung and trachea tissue were obtained from the right lower lobe of the lung and trachea. Specimens were frozen, sectioned to a 5 micron width and stained with DAB peroxidase.

Results are expressed in the Table below as percent cosinophils compared to total leukocytes (inflammatory infiltrate) in each sample, except for the "lung" results, which represent the number of eosinophils per microscopic field (5 randomly selected fields were evaluated for each sample). In summary, the control mice had an average of 67% eosinophils in the lung/trachea tissue samples, while mice who received the mutant ISS-ODN (M-ISS-ODN; DY1019) had 52% and 88% (±12%) average accumulation of eosinophils in lung tissue after IP and 1N administration, respectively. The higher values for the mice treated with M-ISS-ODN after antigen challenge is most likely owing to the immunoinhibitory properties of DY1019 (see, the co-pending, commonly owned U.S. Patent Application entitled "Inhibitors of DNA Immunostimulatory Sequence Activity"; Eyal Raz, inventor; filed Jun. 6, 1997 (Ser. No. 60/048,793 )). Mouse sets 7 and 8 therefore model an partially immune incompetent host with allergic asthma.

In startling contrast, the mice pre-treated with the DY1108 ISS-ODN delivered intranasally had less than about 10% eosinophil accumulation in the lung and trachea when treated after antigen challenge and only about 19% eosinophil accumulation when treated before antigen challenge. These values represent up to an 80% reduction in eosinophil accumulation compared to the control mice and more than a 90% reduction in comparison to M-ISS-ODN (IN) treated mice.

The IP ISS-ODN treated mice fared even better, with a 6% eosinophil accumulation in the lung and trachea on treatment before and after antigen challenge. This value represents an 86% reduction in eosinophil accumulation as compared to the control mice and an 91% reduction as compared to MISS-ODN (IP) treated mice.

These data indicate that the IL-5 stimulated eosinophil accumulation in lung tissue which characterizes the late phase of allergic asthma is inhibited by the ISS-ODN therapeutic methods of the invention.

| Set # | Bone Marrow | Broncheoalveolar Lavage | Blood | Lung and Tracheal Tissue |
|---|---|---|---|---|
| 1 (naive) | 3 ± 2 | 0 | 2 ± 1 | 2 ± 1 |
| 2 (ISS) | 5 ± 1 | 10 ± 2 | 3 ± 1 | 8 ± 1 |
| 3 (ISS) | 12 ± 1 | 17 ± 4 | 6 ± 2 | 19 ± 5 |
| 4 (ISS) | 5 ± 1 | 3 ± 1 | 2 ± 1 | 6 ± 1 |
| 5 (ISS) | 8 ± 2 | 4 ± 3 | 3 ± 1 | 6 ± 4 |
| 6 (ISS) | 10 ± 1 | 10 ± 1 | 4 ± 1 | 16 ± 4 |
| 7 (M-ISS) | 13 ± 1 | 51 ± 3 | 10 ± 1 | 88 ± 12 |
| 8 (M-S) | 13 ± 1 | 43 ± 3 | 10 ± 1 | 52 ± 14 |
| 9 (control) | 3 ± 2 | 42 ± 4 | 14 ± 3 | 67 ± 5 |

EXAMPLE III
Antigen Independent Reduction of Eosinophil Accumulation in Lung Tissue To evaluate whether the eosinophil suppression demonstrated by the data in Example II is dependent upon immune stimulation by the ISS-ODN, mice were sensitized to OVA using a conventional, Th2 stimulatory adjuvant (alum), treated with ISS-ODN or a control, and measured for eosinophil suppression before ISS-ODN stimulation of the mouse immune system would be expected to occur.

More specifically, groups of four mice were immunized with 25 gg OVA in 1 mg alum by subcutaneous injection on days 1, 7, 14 and 21. This immunization protocol is known to stimulate a Th2 type response to the antigen in mice. On day 27, one group of animals received 100 gg of the DY1018 ISS-ODN described in Example I by intraperitoneal administration. A control group received the mutant DY1019 M-ISS-ODN described in Example I by the same route.

On day 28, the animals in each group received 10 mg OVA/ml phosphate buffered saline by inhalation for 30 minutes. On day 30, some of the animals in each group received a second injection of ISS-ODN or M-ISS-ODN and the animals who had not been treated on day 27 were treated with ISS-ODN or MISS-ODN. The inhalation challenge with OVA was repeated on day 31 and the animals were sacrificed for eosinophil counting within 24 hours.

The results of this experiment are set forth in the Table below. Animals that received two treatments with ISS-ODN on days 27 and 30 had only 5.8% eosinophils in the broncheo-alevolar fluid (BALF) lavage on day 32, even though immune stimulation by the ISS-ODN would be minimal so shortly after treatment. Even after only one treatment with ISS-ODN (on day 30), eosinophil accumulation in the BALF the treated animals was limited to 10.3%. In contrast, the control animals twice treated with MISS-ODN had 42.3% eosinophils in extracted BALF.

| Animals | Treated on Day 28 | Blood | Bone Marrow | BALF |
|---|---|---|---|---|
| ISS-ODN | Yes | 1.9% ± 0.8 | 5.8% ± 2.5 | 5.8% ± 2.8 |
| M-ISS-ODN | Yes | 9.8% ± 2.1 | 13.0% ± 0.9 | 42.3% ± 3.5 |
| ISS-ODN | No | 3.5% ± 0.6 | 10.5% ± 1.4 | 10.3% ± 1.3 |

These data establish that practice of the invention can inhibit allergic inflammation in animals and that the inhibition can occur as quickly as one day after treatment.

EXAMPLE IV
Selective Induction of a Th1 Response in a Host after Administration of an ISS-ODN Containing Plasmid In mice, IgG 2A antibodies are serological markers for a Th1 type immune response, whereas IgG 1 antibodies are indicative of a Th2 type immune response. Th2 responses include the allergyassociated IgE antibody class; soluble protein antigens tend to stimulate relatively strong Th2 responses. In contrast, Th1 responses are induced by antigen binding to macrophages and dendritic cells.

To determine which response, if any, would be produced by mice who received ISS-ODN according to the invention, nine groups of Balb/c mice were immunized with 10~,g P-galactosidase protein (conjugated to avidin; Sigma, St. Louis, Mo.) to produce a model allergic phenotype and treated as follows:

| Mouse Group | ISS-ODN Treatment |
|---|---|
| 1 | None (β-gal) |
| 2 | DY1018 (ISS-ODN) injected with the antigen |
| 3 | DY1018 injected 72 hrs. after the antigen (same site) |
| 4 | DY1019 (M-ISS-ODN) injected with the antigen |
| 5 | DY1019 injected 72 hrs. after the antigen (same site) |

At 2 week intervals, any IgG 2a and IgG 1 to (3-galactosidase present in the serum of each mouse were measured by enzyme-linked immunoabsorbent assay (using antibodies specific for the IgG 1 and IgG 2A subclasses) on microtiter plates coated with the enzyme.

Figure 2:
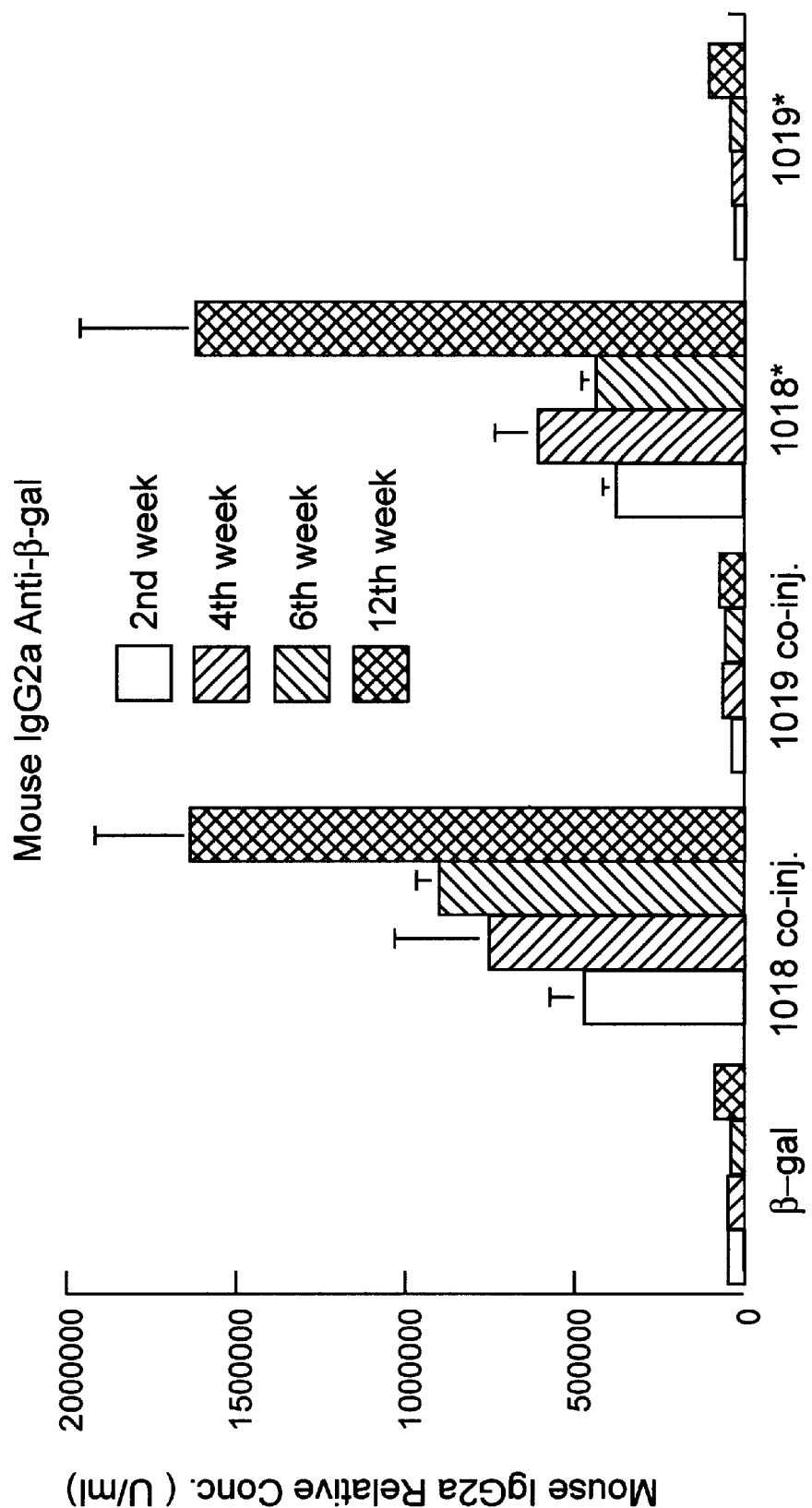
FIG. 2 is a graph of data which confirm a shift from a Th2 to a Th1 phenotype (as measured by IgG2A production) in mice treated with an ISS-ODN 3 days before antigen challenge.
Figure 3A:
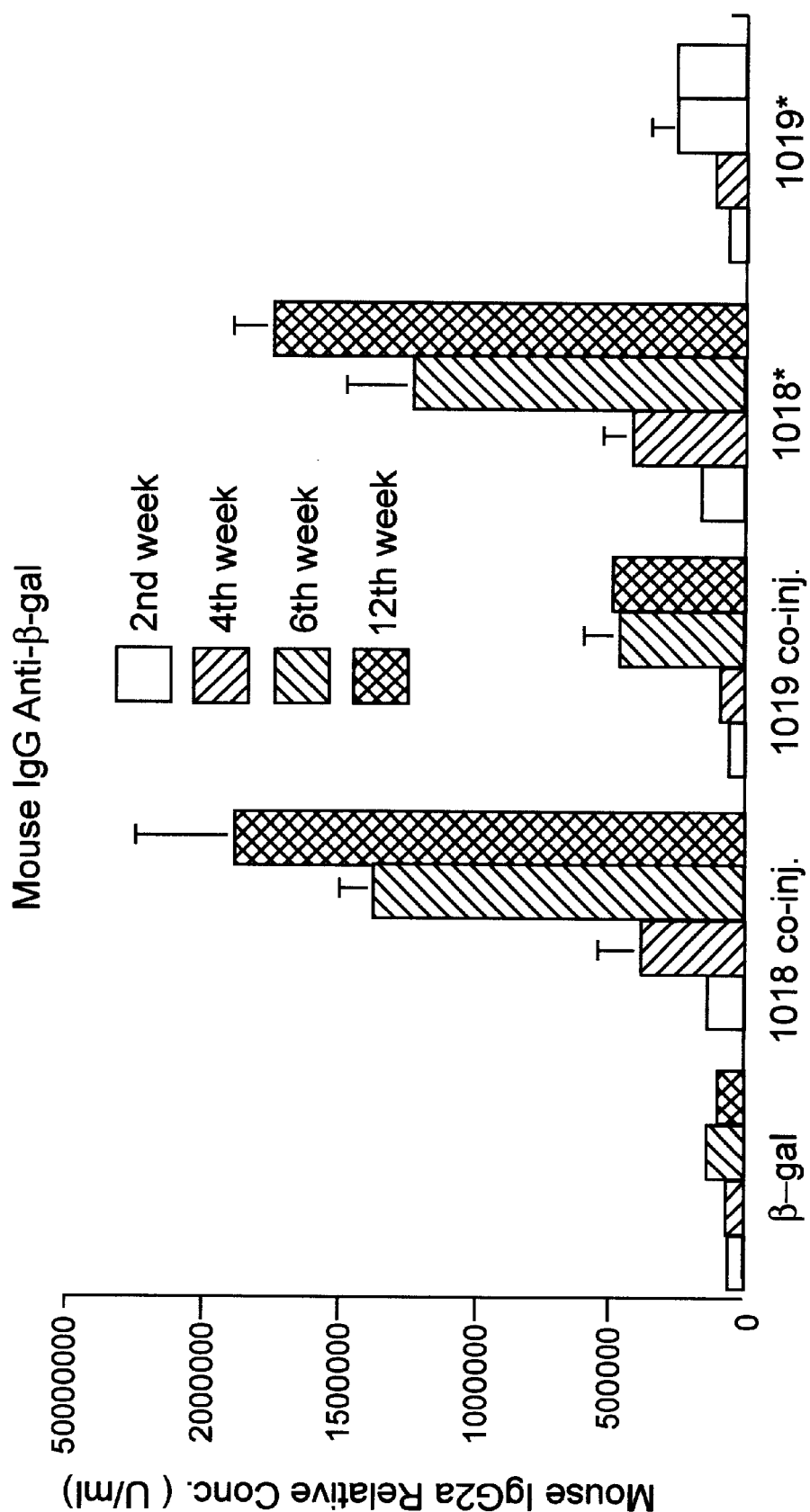
FIGS. 3a and 3b are graphs of data which confirm the induction of a Th2 phenotype (as measured by IgG1 production) in mice treated with a mutant, inactive ISS-ODN 3 days before antigen challenge.
Figure 3B:
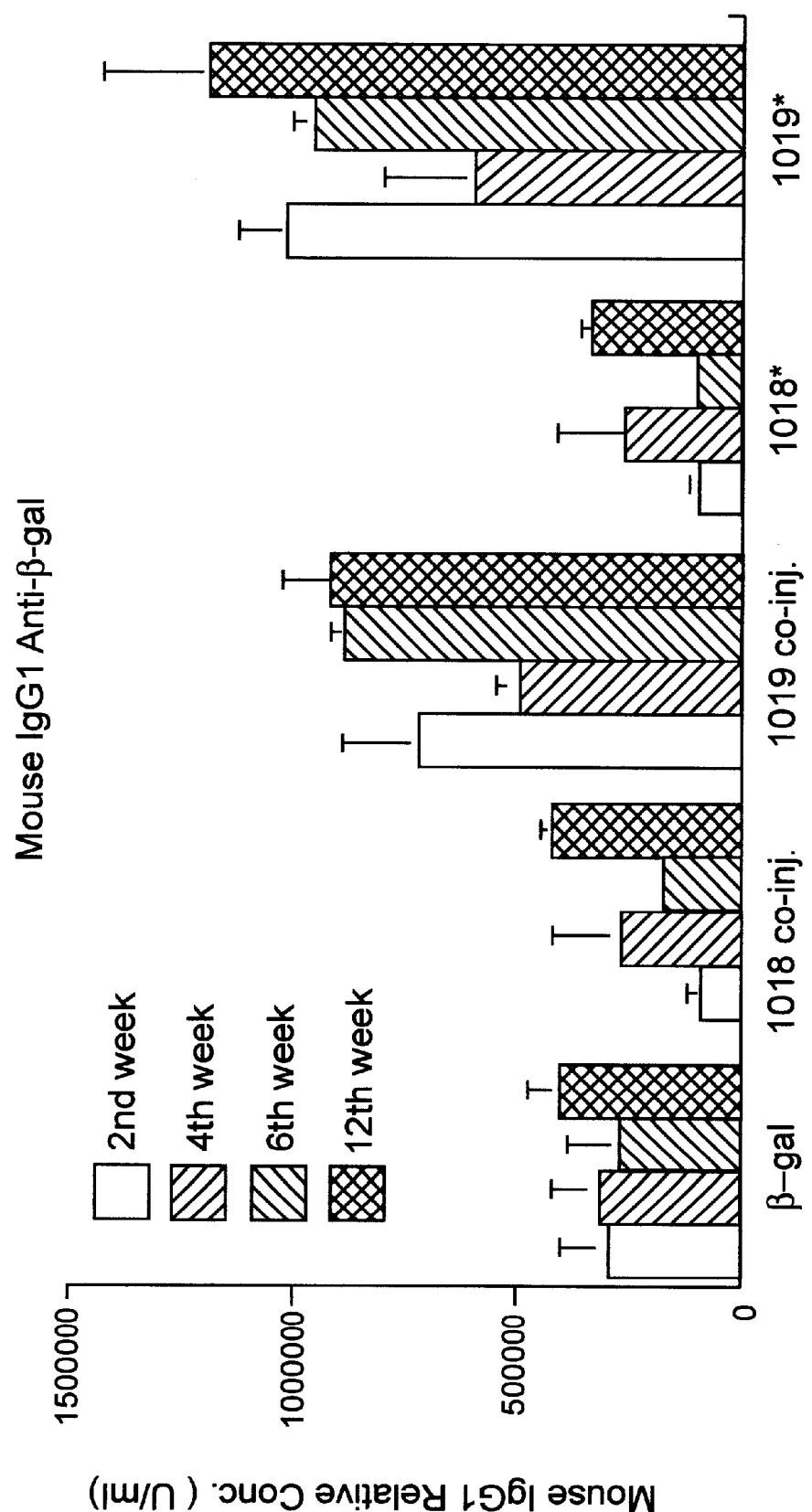

As shown in FIG. 2, only the mice who received the ISS-ODN produced high titers of IgG 2A antibodies, which increased in number over a period of 12 weeks. As shown in FIG. 3, immunization of the mice with the antigen itself or with the mutant ISS-ODN induced production of relatively high titers of IgG 1 antibodies. The data shown in the FIGURES comprise averages of the values obtained from each group of mice.

These data indicate that a selective Th1 response is induced by administration of an ISS-ODN according to the invention to an antigen-challenged host. Further, the data indicate that ISS-ODN administration according to the invention biases the immune system toward the Th1 phenotype on antigen challenge, even when the ISS-ODN are administered before antigen challenge (in this instance, 72 hours before challenge).

EXAMPLE V
Suppression of IgE Antibody Response to Antigen by Immunization with Antigen-encoding Polynucleotides To demonstrate the IgE suppression achieved through stimulation of a Th1 type cellular immune response in preference to a Th2 type cellular immune response, five to eight week old Balb/c mice were immunized with one of two recombinant expression vectors: ISS-ODN containing pCMV-LacZ (which contains two copies of nucleotide sequences similar to the DY1018 ISS-ODN) or a control plasmid, pCMV-BL. A third group of the mice received injections of antigen (β galactosidase). Plasmid DNA was purified and its endotoxin content reduced to 0.5–5 ng/1 mg DNA by extraction with TRITON X-114 (Sigma, St. Louis, Mo. Before inoculation, pDNA was precipitated in ethanol, washed with 70% ethanol and dissolved in pyrogen free normal saline.

Immunization was by intradermal injection of plasmid DNA loaded onto separate tynes of a MONOVACC® multiple tyne device (Connaught Lab, Inc., Swiftwater, Pa.). Briefly, the tyne devices were prepared after extensive washing in DDW and overnight soaking in 0.5% SDS (sulfated dodecyl saline), washed again in DDW, soaked overnight in 0.1N NaOH, washed again in DDW and dried at 37° C. for 8 hours. Six $\mu$l of plasmid DNA dissolved in normal saline were pipetted onto the tynes of the tyre device just prior to each inoculation described below. The total amount of pDNA loaded on the device per inoculation was 25 $\mu$g each of pCMV-Lac-Z and pCMV-BL. For purposes of estimating actual doses, it was assumed that less than 10% of the pDNA solution loaded onto the tyre device was actually introduced on injection of the tynes into intradermal tissue.

Each mouse was treated 3 times with 2 inoculations of each plasmid in a one week interval injected intradermally at the base of the tail. Another group of mice received a single intradermal injection in the base of the tail of 10 pg of β galactosidase protein (dissolved in 50 $\mu$l of normal saline) in lieu of pDNA.

Toward inducing an IgE antibody response to subsequent sensitizing-antigen challenge, each group of mice was injected once intraperitoneally with 0.1 ml of phosphate buffered saline (PBS) solution containing 1 $\mu$g of antigen (β galactosidase; Calbiochem, San Diego, Calif.) and 3 mg of ALUM aluminum hydroxide as adjuvant (Pierce Chemical, Rockford, Ill.) 14 weeks after the initial immunization. Total IgE was assayed in sera from the mice 4 times over the subsequent 4 consecutive weeks.

IgE was detected using a solid phase radioimmunoassay (RAST) in a 96 well polyvinyl plate (a radioisotopic modification of the ELISA procedure described in Coligan, "Current Protocols In Immunology", Unit 7.12.4, Vol. 1, Wiley & Sons, 1994), except that purified polyclonal goat antibodies specific for mouse E chains were used in lieu of antibodies specific for human Fab. To detect antiLac-Z IgE, the plates were coated with β galactosidase (10 $\mu$g/ml). The lowest IgE concentration measurable by the assay employed was 0.4 ng of IgE/ml.

Figure 4:
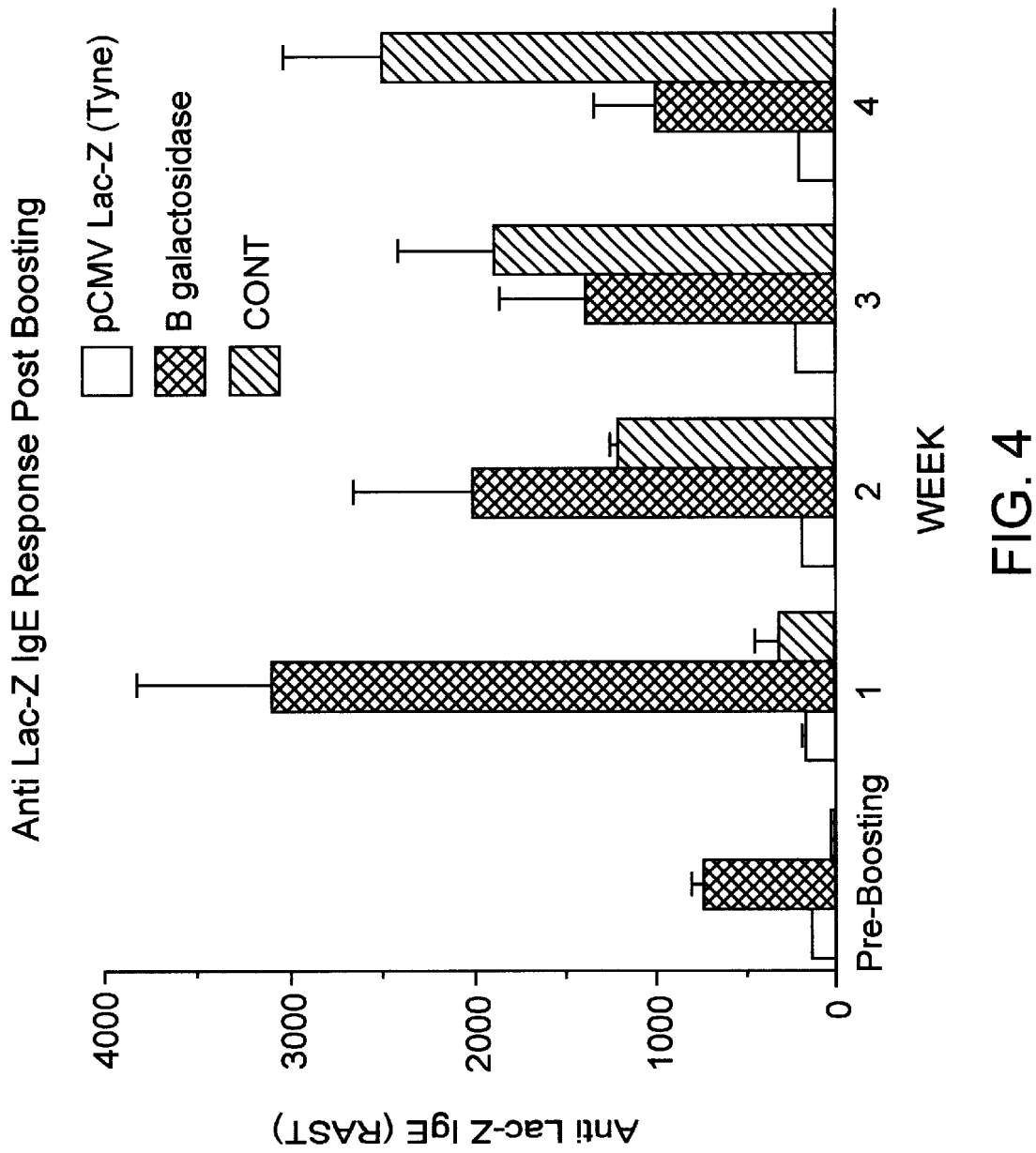
FIG. 4 is a graph of data which confirm Th1-associated suppression of antigen-specific IgE in antigensensitized, ISS-ODN (pCMV-LacZ, a plasmid containing two copies of the DY1018 ISSODN)treated mice as compared to antigen-sensitized (control) mice.

Measuring specifically the anti-antigen response by each group of mice, as shown in FIG. 4, anti-Lac-Z IgE levels in the ISS-ODN containing plasmid injected mice were consistently low both before and after boosting (averaging about 250 CPM in RAST), while the protein injected mice developed high levels of anti-Lac-Z, particularly after the first antigen booster injection, when antiLac-Z levels in the mice rose to an average of about 3000 CPM. Consistent with acquisition of tolerance, anti-Lac-Z IgE levels in the protein injected mice declined over time, but continued to rise in the control mice who had not received any immunization to β galactosidase.

These data show that the ISS-ODN containing plasmid injected mice developed an antigen specific Th1 response to the plasmid expression product with concomitant suppression of IgE production, while tolerance was acquired in the protein injected mice only after development of substantially higher levels of antigen specific IgE antibodies.

EXAMPLE VI

IL-4, IL-5, IL-10 and INFy Levels, and CD4+ Lymphocyte Proliferation, in Mice after Delivery of ISS-ODN BALB/c mice were injected intravenously with 100 gg of DY1018, DY1019 or a random sequence control (DY1043) then sacrificed 24 hrs later. Splenocytes were harvested from each mouse.

96 well microtiter plates were coated with anti-CD3 antibody (Pharmingen, La Jolla, Calif.) at a concentration of 1 pg/ml of saline. The anti-CD3 antibody stimulates T cells by delivering a chemical signal which mimics the effects of binding to the T cell receptor (TCR) complex. The plates were washed and splenocytes added to each well ($4\times10^5$/well) in a medium of RPMI 1640 with 10% fetal calf serum. Supernatants were obtained at days 1, 2 and 3.

Th2 cytokine (IL-4, IL-5 and IL-10) levels were assayed in the supernatants using a commercial kit; Th1 cytokine (INFγ) levels were assayed with an anti-INFγ murine antibody assay (see, e.g., Coligan, "Current Protocols in Immunology", Unit 6.9.5., Vol. 1, Wiley & Sons, 1994). Relatively high levels of IL-4 and IL-10 with low levels of INF-γ would be expected in mice with a Th2 phenotype, while relatively low levels of IL-4 and IL-10 with high levels of INF-γ would be expected in mice with a Th1 phenotype. Relatively high levels of IL-5 characterize a proinflammatory mileau, while the converse is true of relatively low levels of IL-5.

Figure 5:
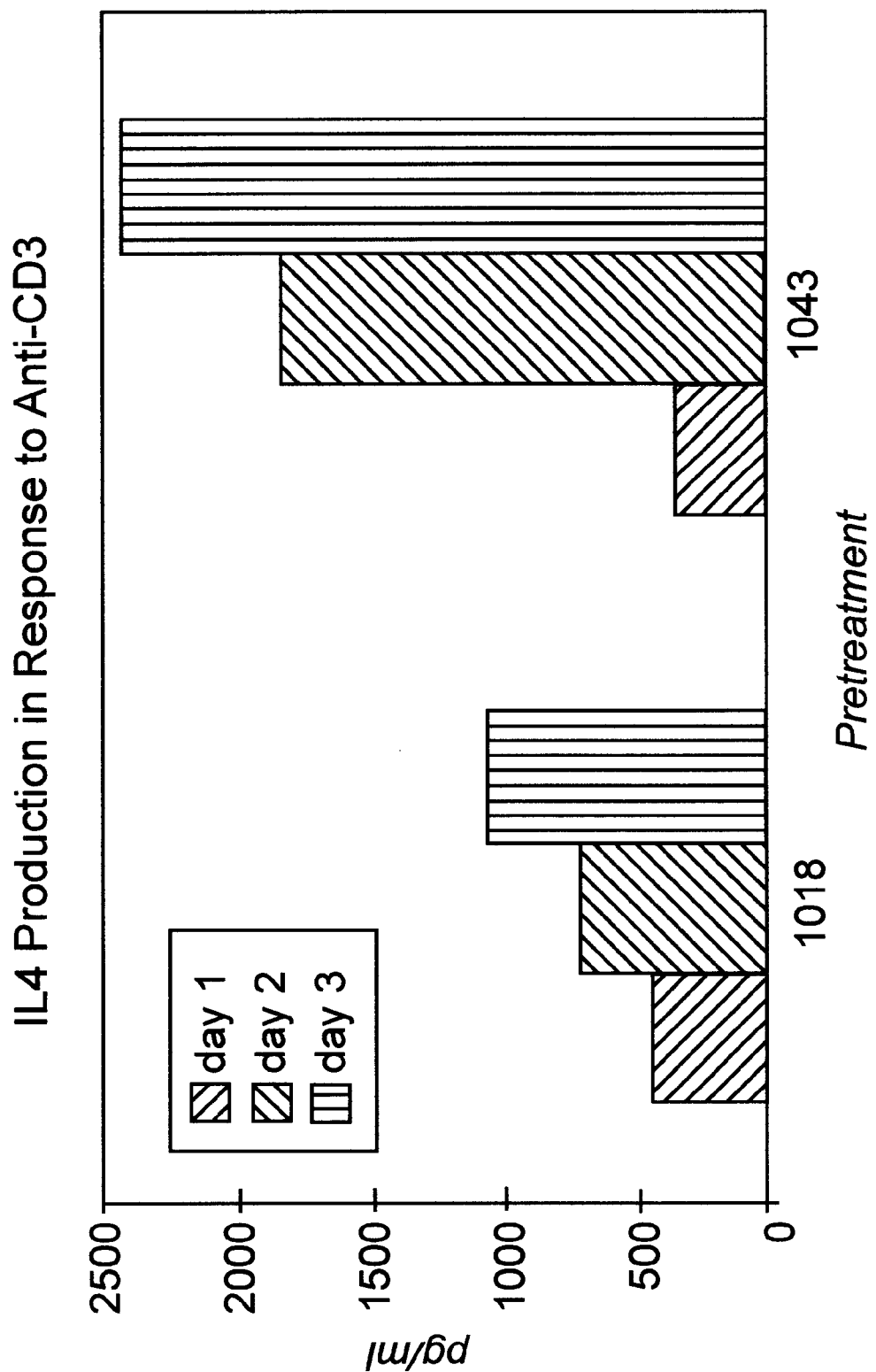
FIG. 5 is a graph of data which confirm suppression of IL-4 secretion by ISS-ODN as compared to a control.
Figure 6:
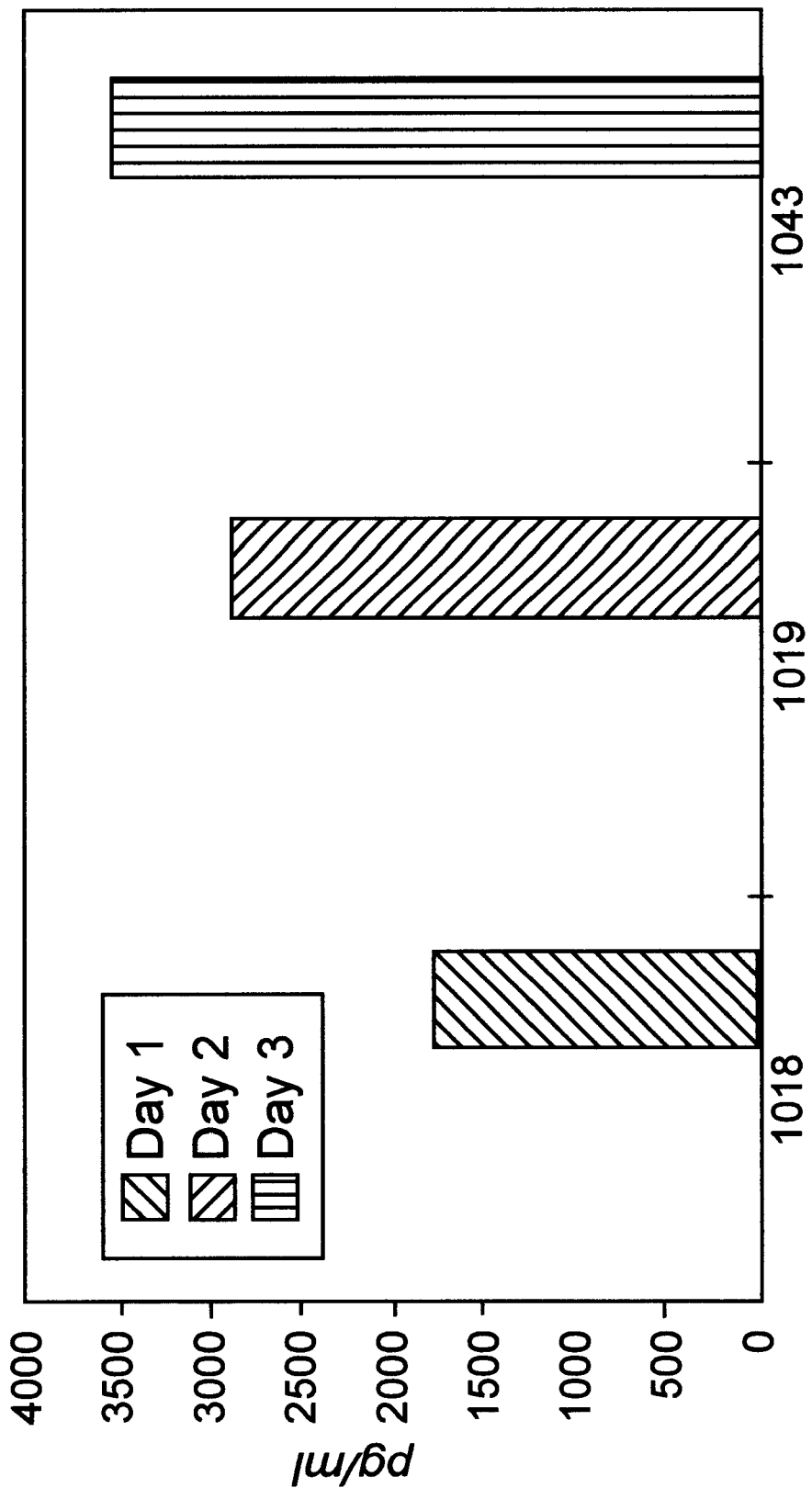
FIG. 6 is a graph of data which confirm suppression of IL-5 secretion by ISS-ODN as compared to a control.
Figure 7:
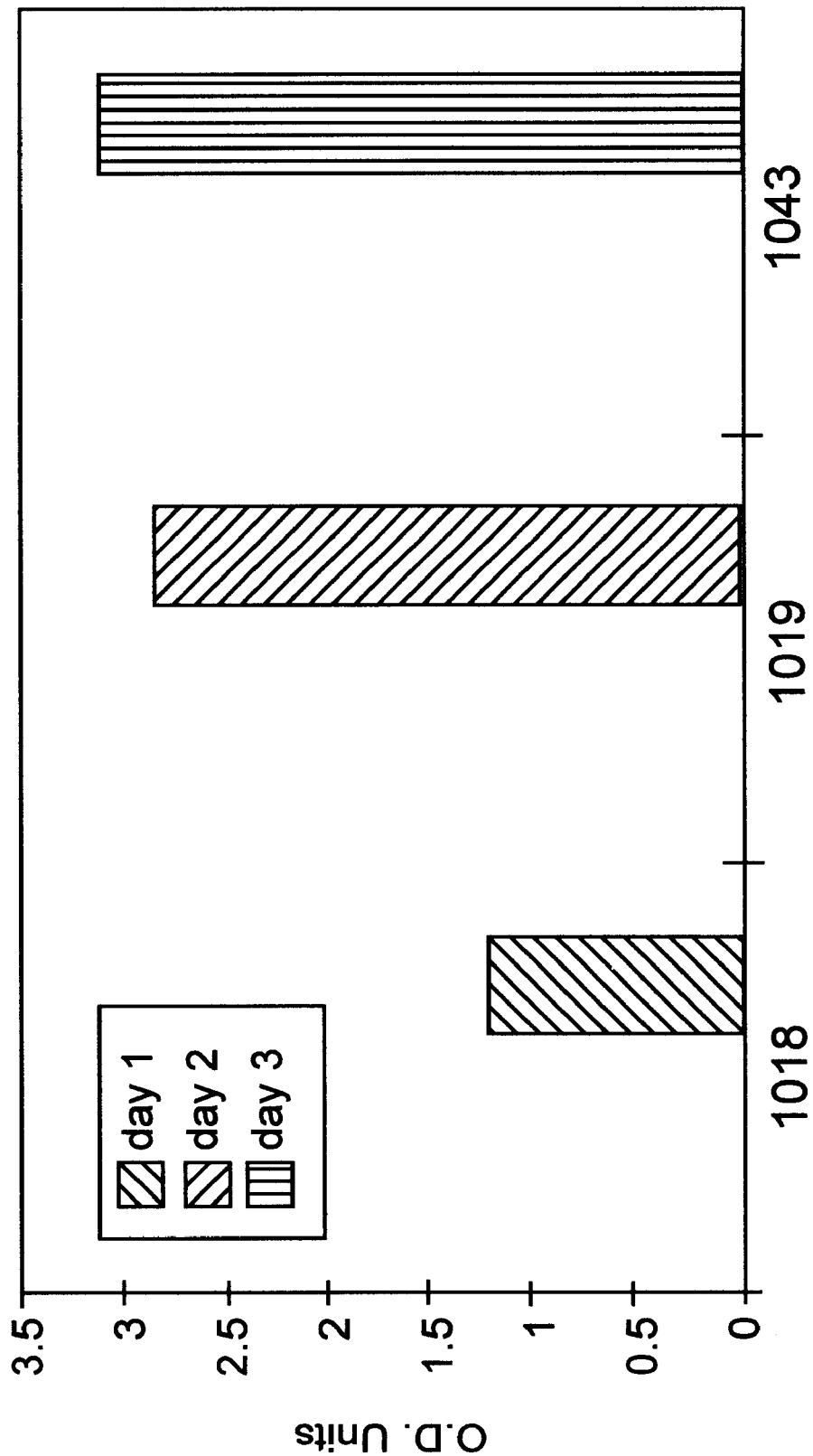
FIG. 7 is a graph of data which confirm suppression of IL-10 secretion by ISS-ODN as compared to a control.

As shown in FIGS. 5 and 6, levels of anti-CD3 stimulated IL-4 and IL-10 secretion in DY1018 treated mice were substantially lower than in the control mice. Levels in the DY1019 mice were intermediate. Levels of proinflammatory IL-5 were reduced in DY1018 treated mice to a comparable extent (FIG. 7).

Levels of T cell proliferation in response to antigen challenge were greatly reduced in DY1018 (ISSODN) treated mice as compared to DY1019 (mutant ISS-ODN) treated and control mice. This suppression of T cell proliferation was reversible on adminstration of IL2, demonstrating that the suppression was due to Th2 anergy in the ISS-ODN treated mice (see, Table below).

| Treatment | Control (CPM) | ISS-ODN (CPM) | M-ODN (CPM) |
| --- | --- | --- | --- |
| OVA (50 $\mu$g/ml) | 40680 ± 5495 | 15901 ± 4324 | 42187 ± 13012 |
| OVA + IL-2 (1.5 ng/ml) | 65654 ± 17681 | 42687 ± 6329 | 79546 ± 10016 |
| OVA-IL-2 (15 ng/ml) | 60805 ± 19181 | 57002 ± 10658 | 60293 ± 5442 |

Figure 8:
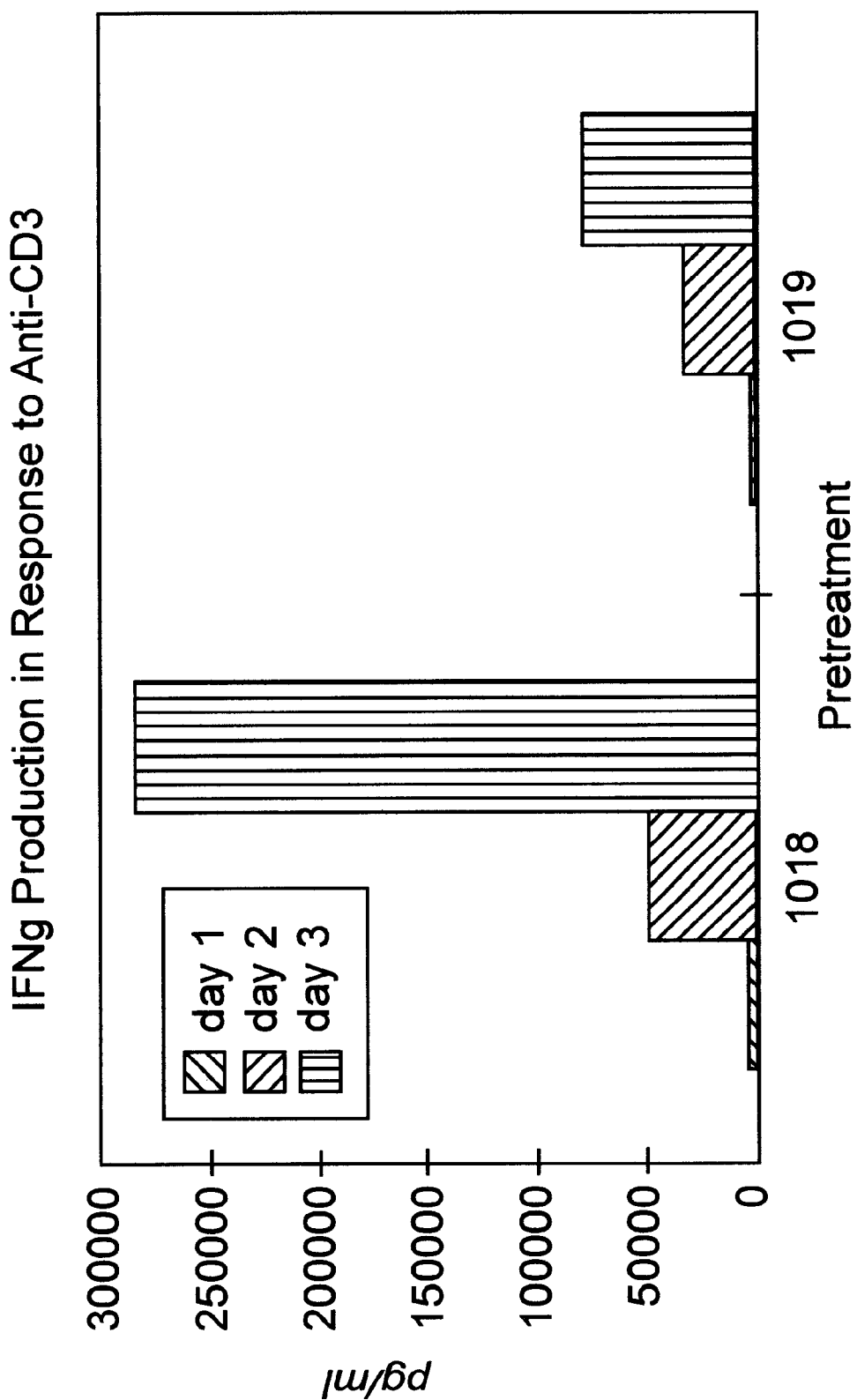
FIG. 8 is a graph of data which confirm stimulation of INF-y secretion by ISS-ODN as compared to a control.

Levels of Th1 stimulated IFN-γ secretion were greatly increased in the DY1018 treated mice, but substantially reduced in the DY1019 treated mice (as compared to the control), indicating stimulation of a Th2-type mileau in the latter mice (FIG. 8). Additional data demonstrating these results are shown in the Table below. "b/fl' in the Table refers to before; "1 st", "2nd" and "each" refer to administration of the compound before the 1 st or 2nd antigen challenge.

Figure 9:
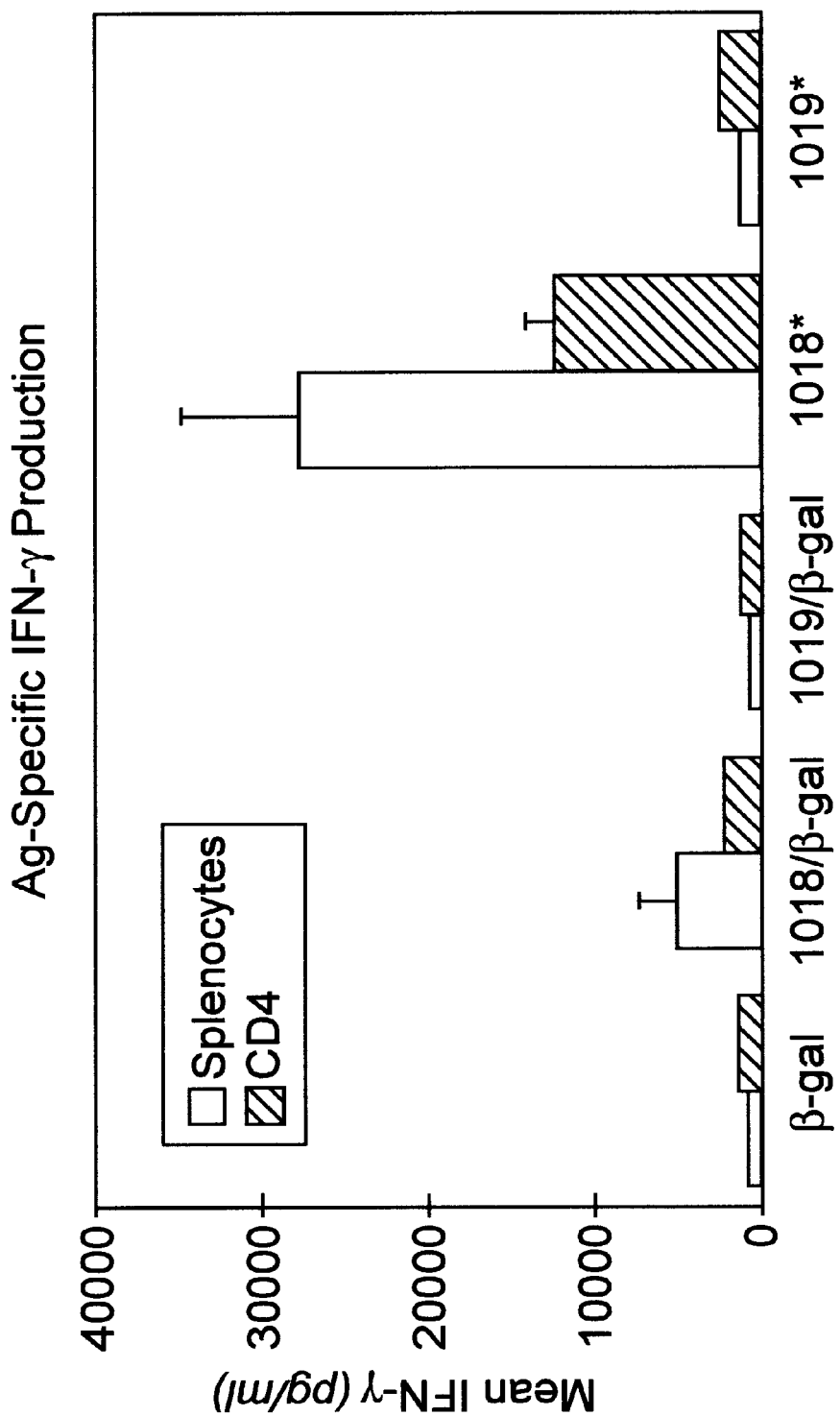
FIG. 9 is a graph of data demonstrating an ISS-ODN mediated shift to a Th1 phenotype (as indicated by IFNy levels) in animals treated with ISS-ODN before antigen challenge (asterisked bars) or after antigen challenge.
Figure 10:
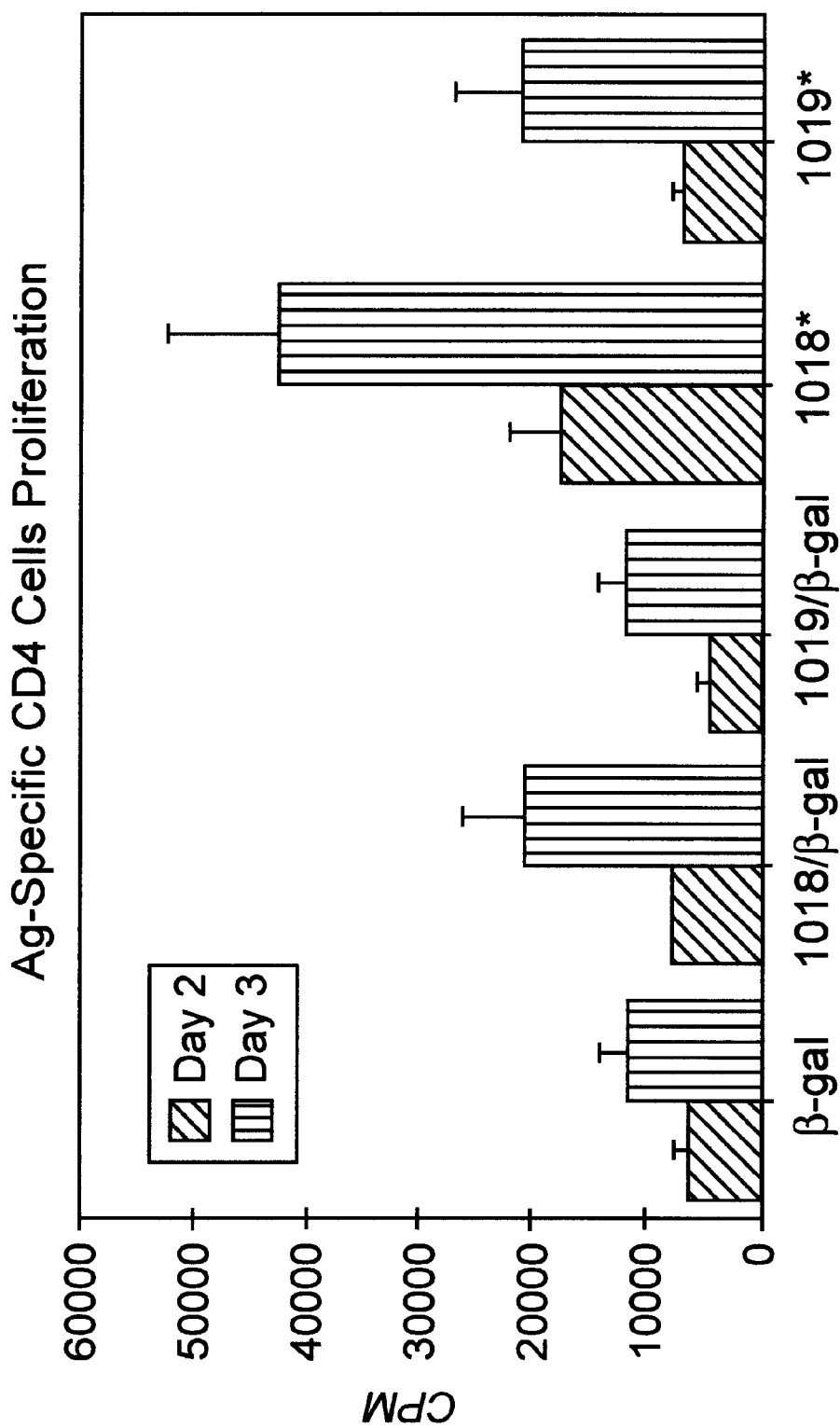
FIG. 10 is a graph of data demonstrating an ISS-ODN mediated boost in immune responsiveness (as indicated by increases in CD4+ lymphocyte proliferation) in animals treated with ISS-ODN before antigen challenge (asterisked bars) or after antigen challenge.

Importantly, treatment of mice before antigen challenge is even more effective in shifting the immune response on antigen challenge to a Th1 phenotype than is post-challenge treatment. As shown in FIGS. 9 and 10, antigen primed (but unchallenged) animals injected with IS S-ODN DY1019 72 hours before antigen challenge (with β galactosidase) mounted a more robust Th1-type immune response to the antigen than did their post-challenge treated littermates or littermates treated pre-challenge with a mutant, inactive oligonucleotide (DY1019), as measured by increased IFN-γ secretion (FIG. 9) and CD4+ lymphocyte proliferation (FIG. 10).

| Set # | IL-5(pg/ml) | IFN-γ(pg/ml) |
|---|---|---|
| 1 (naive) | <20 | <20 |
| 2 (ISS) in b/f 1st | 466 ± 40 | 246 ± 86 |
| 3 (ISS) b/f 2nd | 531 ± 109 | 168 ± 22 |
| 4 (ISS) in with 2nd | 575 ± 90 | 98 ± 44 |
| 5 (ISS) in b/f each | 200 ± 66 | 443 ± 128 |
| 6 (ISS) ip; b/f 1st | 190 ± 52 | 664 ± 61 |
| 7 (ISS) ip; b/f 2nd | 421 ± 102 | 252 ± 24 |
| 8 (ISS) ip; with 2nd | 629 ± 110 | 104 ± 15 |
| 9 (ISS) ip; b/f each | 121 ± 18 | 730 ± 99 |
| 10 (ISS) it; b/f each | 191 ± 49 | 610 ± 108 |
| 11 (M-ISS) in; b/f each | 795 ± 138 | 31 ± 22 |
| 12 (M-ISS) it; b/f each | 820 ± 122 | 33 ± 33 |
| 13 (M-ISS) it; b/f each | 657 ± 52 | 102 ± 57 |
| 14 (steroid) sc; b/f each | 424 ± 90 | <20 |
| 15 (steroid) sc; daily | 252 ± 96 | <20 |
| 16 (control) not treated | 750 ± 124 | 24 ± 21 |

Further, ISS-ODN administered according to the invention suppress Th2 cytokine release from Th2 sensitized mouse cells (splenocytes harvested from OVA-primed mice, then incubated for 72 hours with 100 μg/ml OVA in vitro). IS SODN treatment took place either 1 (−1) or 3 (−3) days before sacrifice. These data are shown below:

| Group | IL-3 (pg/ml) | IL-5 (pg/ml) | IFN-γ (pg/ml) |
|---|---|---|---|
| Control | 1299 ± 89 | 657 ± 52 | <20 |
| ISS-ODN (−1) | 309 ± 26 | 112 ± 18 | <20 |
| ISS-ODN (−3) | 463 ± 48 | 144 ± 27 | <20 |
| ISS-ODN (−1) | 964 ± 81 | 508 ± 77 | <20 |

SEQUENCE LISTING

SEQUENCE ID Nos. 1 through 18 are representative hexameric nucleotide sequences of ISS-ODN.

SEQUENCE ID No. 19 is the complete nucleotide sequence of IS S-ODN DY1018.

SEQUENCE ID No. 20 is the complete nucleotide sequence of an inactive ISS-ODN mutant, DY1019.

The invention claimed is:

1. A method for treating asthma, comprising:
administering to a mammal sensitized to an asthma-stimulating antigen an immunostimulatory polynucleotide comprising an immunostimulatory sequence (ISS), wherein the ISS comprises the sequence 5'-cytosine-guanine-3', wherein the immunostimulatory polynucleotide does not comprise a nucleotide sequence encoding the antigen, and wherein the immunostimulatory polynucleotide is administered without the antigen, including without a polynucleotide encoding the antigen, and in an amount sufficient to treat asthma.

2. The method of claim 1, wherein the ISS comprises the sequence 5'-purine-purine-cytosine-guanine-pyrimidine-pyrimidine-3'.

3. The method of claim 2, wherein the ISS comprises the sequence 5'-AACGTT-3'.

4. The method of claim 2, wherein the ISS comprises a nucleotide sequence selected from the group consisting of AGCGTC, GACGTT, GGCGTT, AACGTC, GACGTC, GGCGTC, AGCGCC, GACGCC, GGCGCC, AGCGCT, GACGCT, GGCGCT, AACGCT, AACGTT, AGCGTT, and AACGCC.

5. The method of claim 1, wherein the ISS comprises SEQ ID NO:19.

6. The method of claim 2, wherein the ISS comprises a nucleotide sequence selected from the group consisting of AGCGUC, GACGUU, GGCGUU, AACGUC, GACGUC, GGCGUC, AGCGCC, GACGCC, GGCGCC, AGCGCU, GACGCU, GGCGCU, AACGCU, AACGUU, AGCGUU, AACGCC, GACGUT, GACGTU, GGCGUT, GGCGTU, AACGUT, AACGTU, AGCGUT, and AGCGTU.

7. The method of claim 1, wherein the immunostimulatory polynucleotide is administered intramuscularly.

8. The method of claim 1, wherein the immunostimulatory polynucleotide is administered to skin.

9. The method of claim 1, wherein the immunostimulatory polynucleotide is administered to respiratory tissue.

10. The method of claim 1, wherein the immunostimulatory polynucleotide is linked to a peptide, wherein said peptide is not the antigen to which the mammal is sensitized.

11. The method of claim 10, wherein the peptide is a targeting moiety.

12. The method of claim 10, wherein the peptide is a cytokine.

13. The method of claim 1, wherein the immunostimulatory polynucleotide is linked to an antibody.

14. The method of claim 1, further comprising administering an immunotherapeutic agent.

15. The method of claim 1, further comprising administering an anti-inflammatory agent.

16. The method of claim 1, wherein eosinophil accumulation in lung tissue is reduced.

17. The method of claim 1, wherein the ISS is at least six nucleotides in length.

18. The method of claim 1, wherein inflammation stimulated by the asthma-stimulating antigen is reduced.

19. The method of any one of claim 1, 2, 3, 4, 5, or 17, wherein the mammal is a human.

* * * * *

Adverse Decision in Interference

Patent No. 6,498,148, Eyal Raz, IMMUNIZATION-FREE METHODS FOR TREATING ANTIGEN-STIMULATED INFLAMMATION IN A MAMMALIAN HOST AND SHIFTING THE HOST'S ANTIGEN IMMUNE RESPONSIVENESS TO A TH1 PHENOTYPE, Interference No. 105,674, final judgment adverse to the patentees rendered May 20, 2009, as to claim 58.
*(Official Gazette, January 12, 2010)*

Adverse Decision in Interference

Patent No. 6,498,148, Eyal Raz, IMMUNIZATION-FREE METHODS FOR TREATING ANTIGEN-STIMULATED INFLAMMATION IN A MAMMALIAN HOST AND SHIFTING THE HOST'S ANTIGEN IMMUNE RESPONSIVENESS TO A TH1 PHENOTYPE, Interference No. 105,526, final judgment adverse to the patentees rendered December 1, 2008, as to claims 1-4, 6-19.

(*Official Gazette, April 27, 2010*)